US007712899B2

(12) United States Patent
Tanassi et al.

(10) Patent No.: US 7,712,899 B2
(45) Date of Patent: May 11, 2010

(54) DUAL SCHEIMPFLUG SYSTEM FOR THREE-DIMENSIONAL ANALYSIS OF AN EYE

(75) Inventors: Cesare Tanassi, Susegana (IT); Walter Zanette, San Fior (IT); Irene Mogentale, Lendinara (IT); Gianluigi Meneghini, Selvazzano Dentro (IT)

(73) Assignee: SIFI Diagnostic SpA, Treviso (IT)

( * ) Notice: Subject to any disclaimer, the term of this patent is extended or adjusted under 35 U.S.C. 154(b) by 0 days.

(21) Appl. No.: 12/340,344

(22) Filed: Dec. 19, 2008

(65) Prior Publication Data

US 2009/0190093 A1 Jul. 30, 2009

Related U.S. Application Data

(60) Provisional application No. 61/100,668, filed on Sep. 26, 2008, provisional application No. 61/016,424, filed on Dec. 21, 2007.

(51) Int. Cl.
*A61B 3/14* (2006.01)
*A61B 3/10* (2006.01)
*A61B 3/00* (2006.01)

(52) U.S. Cl. ........................ 351/206; 351/208; 351/209; 351/221; 351/246

(58) Field of Classification Search ................. 351/200, 351/205, 206, 208, 209, 221, 246
See application file for complete search history.

(56) References Cited

U.S. PATENT DOCUMENTS 5,341,180 A 8/1994 Isogai et al.

| 5,512,965 | A | 4/1996 | Snook |
| 5,864,382 | A | 1/1999 | Soya et al. |
| 5,870,167 | A | 2/1999 | Knopp et al. |
| 6,286,958 | B1 | 9/2001 | Koest et al. |
| 6,592,574 | B1 | 7/2003 | Shimmick et al. |
| 6,860,602 | B2 | 3/2005 | Sumiya et al. |
| 7,264,355 | B2 | 9/2007 | Rathjen |
| 7,425,068 | B2 * | 9/2008 | Koest .......................... 351/246 |

FOREIGN PATENT DOCUMENTS

WO WO-2004/037077 5/2004

OTHER PUBLICATIONS

International Search Report and Written Opinion for PCT/IB2008/003956, mailed Aug. 4, 2009, 8 pages.
Menassa et al., Journal Cataract and Reactive Surgery (2008) 34(10):1742-1747.
Roberts et al., "The Advantage and Principle of Dual Scheimpflug Imaginng for Analyzing the Anterior Segment of the Human Eye" (2006), retrieved from the Internet: URL:http://www.ziemergroup.ch/fileadmin/media/products/GALILEI/Roberts_Galilei_2006.pdf> [retrieved on Jun. 15, 2009] pp. 1-8.

* cited by examiner

*Primary Examiner*—Jack Dinh
(74) *Attorney, Agent, or Firm*—Levine Bagade Han LLP

(57) ABSTRACT

An apparatus for imaging an eye can include a pair of Scheimpflug imaging systems. Each Scheimpflug imaging system can have respective video cameras and optics configured to direct light reflected from an eye into the video cameras. The apparatus can also have a movable platform configured to move the pair of Scheimpflug imaging systems in accordance with eye movement detected by an eye tracking imaging system. In some embodiments, the Scheimpflug imaging systems can rotate 90 degrees about an optical axis of an eye being examined.

19 Claims, 25 Drawing Sheets

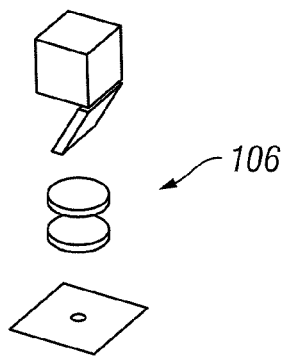
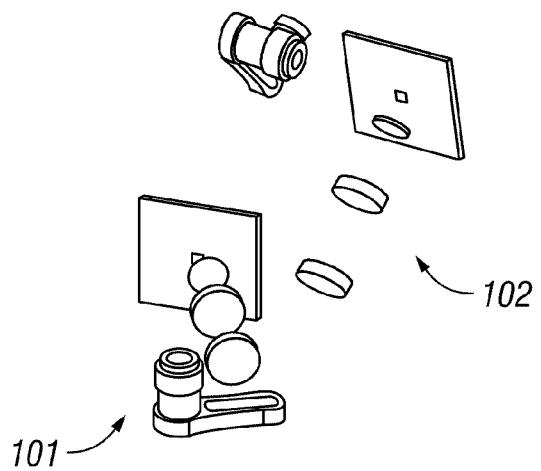
FIG. 2  FIG. 3
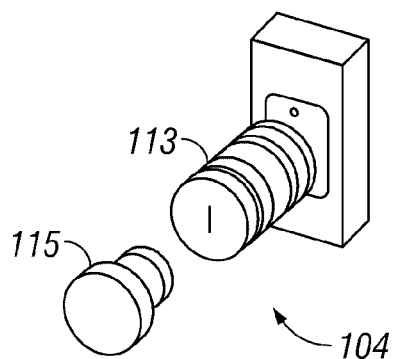
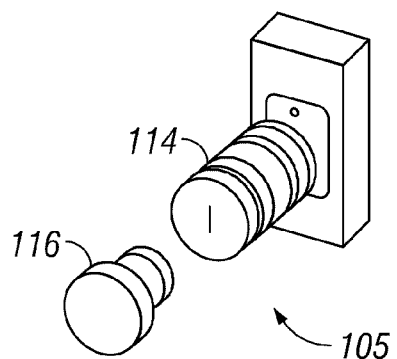
FIG. 4A  FIG. 4B

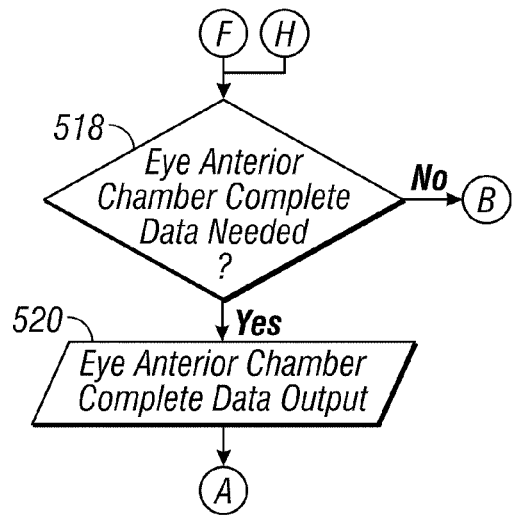
FIG. 5C
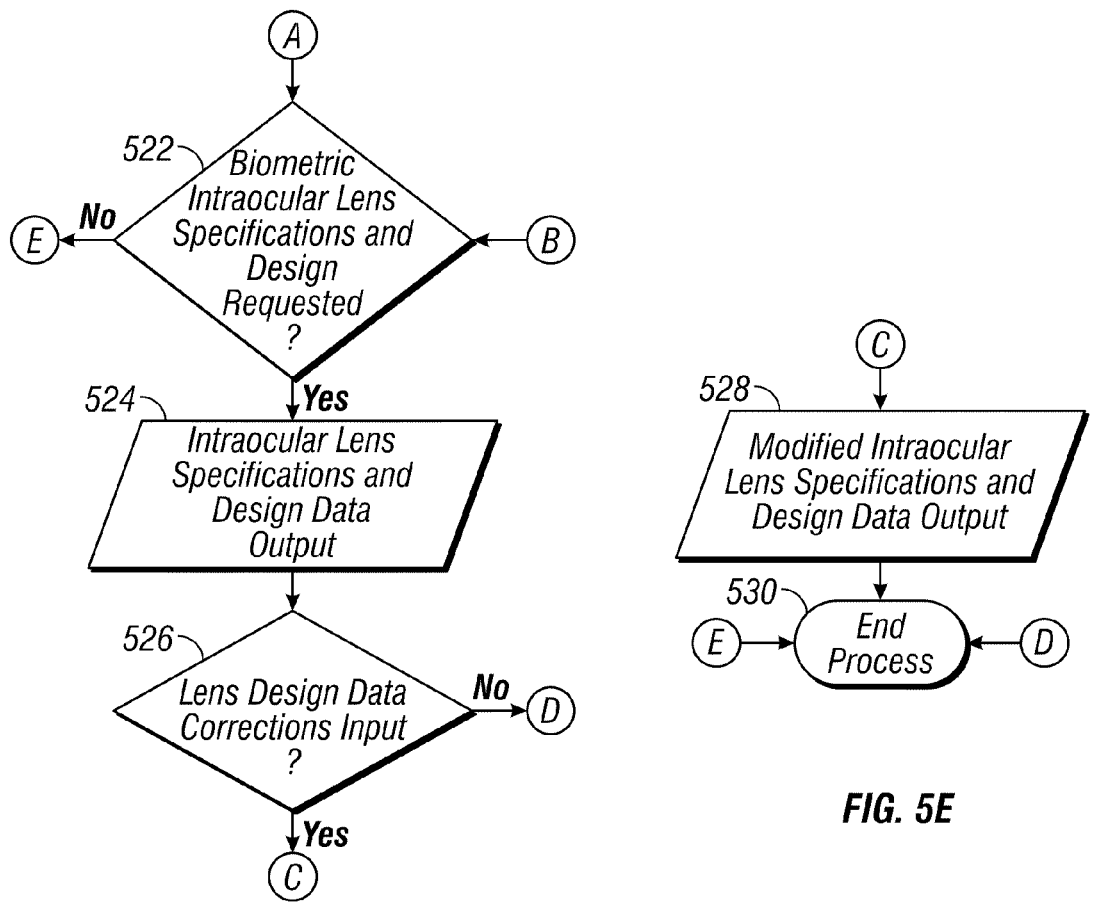
FIG. 5D
FIG. 5E

Optical Axis

Visual Axis

Pupillary Axis

Line of Sight

DUAL SCHEIMPFLUG SYSTEM FOR THREE-DIMENSIONAL ANALYSIS OF AN EYE

PRIORITY INFORMATION

This application claims benefit of priority under 35 U.S.C. § 119(e) to U.S. Provisional Patent Application No. 61/100,668, filed on Sep. 26, 2008, the contents of which are hereby incorporated herein by reference in their entirety.

This application also claims benefit of priority under 35 U.S.C. § 119(e) to U.S. Provisional Patent Application No. 61/016,424, filed on Dec. 21, 2007, the contents of which are hereby incorporated herein by reference in their entirety.

FIELD OF THE INVENTION

This invention relates to system and methods for analyzing an eye, and more particularly, some embodiments relate to imaging portions of an eye using a pair of rotating Scheimpflug cameras positioned perpendicular to one another.

SUMMARY OF THE INVENTION

Topographic mapping of the cornea, generally referred to as keratometry or keratography, can be utilized to both measure the front shape of the cornea and detect corneal shape irregularities. Keratography methods can be developed and coupled with computer-assisted analysis to display derived corneal shapes. Scheimpflug imaging can be a method used for anterior eye segment analysis. The incorporation of a Scheimpflug camera, which can capture Scheimpflug images of the anterior eye segment, can provide sharp and crisp images that can include detailed information from the anterior corneal surface.

Scheimpflug imaging can have one or two rotating Scheimpflug cameras. Scheimpflug imaging can provide a complete analysis of the anterior and posterior surface topography of the cornea, including curvature, tangential, and sagittal (axial) maps. The topography of the anterior and posterior surfaces of the cornea can be generated from a true elevation measurement. The Scheimpflug principle can allow data capture in patients with significant keratoconus and other severe irregularities not detected in other types of imaging (e.g. Placido imaging). The Scheimpflug based methods can calculate the thickness pachymetry of the cornea from limbus to limbus and displays the results in a colored map.

Some embodiments can comprise a fully automatic, non-invasive, ophthalmologic analyzer device. The device can be used to measure anterior and poster corneal curvature and corneal thickness (pachymetry), and anterior chamber volume. The device can also allow real time evaluation of accommodation amplitude.

Some embodiments can include an ophthalmologic device capable of imaging anterior segments of an eye using a pair of rotating Scheimpflug cameras positioned perpendicular to one another. Rotating imaging processing can be used to provide a precise measurement of the central cornea, an easy fixation for the patients and an extremely short examination time. In addition, with a 90-degree rotation, the device can generate a three-dimensional representation of the entire anterior chamber by measuring all surfaces of the anterior segment. Accordingly, a three-dimensional representation of the anterior corneal surface, posterior corneal surface, anterior iris surface and anterior lens surface can be generated and displayed on a monitor. Embodiments of the device can also measure the accommodation of the eye to near and far fixation targets. Data relating to the cornel pachymetry and anterior chamber depth can be displayed on a computer monitor.

Embodiments can also include a tracking camera that detects eye movement and automatically adjusts the alignment of the optical system to minimize the influence of the eye movement. The eye movement can be a result of involuntary reactions by the patient, for example. The optical system can be actively aligned using X/Y/Z auto-alignment mechanics during the measurement process. By using the tracking camera to track and correct eye movement, software-introduced estimates need not be used to measure an anterior segment.

Accordingly, some embodiments can be configured for real-time tracking of an eye via a tracking camera to actively correct the alignment of the optical system. The tracking camera alignment system can include a sensor, an actuator and auto-alignment mechanics for anterior cornea topography analysis and accommodation amplitude measurement.

Some embodiments can comprise a dual Scheimpflug optical system capable of the three-dimensional analysis of the anterior and posterior cornea. The optical system can provide measurements at two orthogonal meridians, thereby allowing a 3-dimensional scan in a 90 degree rotation. Accordingly, the optical system can perform a full surface evaluation in a 90 degree rotation.

Some embodiments can include a fully automatic, noninvasive, real-time eye movement tracking system. The system can include an ergonomic headrest for patient self-alignment, mechanics that allow the real time tracking of the eye via a tracking camera, and auto-alignment mechanics that can move the system in x, y and z dimensions in accordance with detected eye movement.

Some embodiments can be reconstructing an accurate model of an examined eye and providing a functional wavefront analysis with respect to the model. The model can be used to generate a simulated environment for an intraocular lens (IOL) implant, determining manufacturing parameters such as decentration and dimensions of the optical plate and haptics, tilting of the lens, exact fitting into the capsular bag and fixation. The model can also be used for planning other types of refractive surgery in conjunction with the derived topography, pachymetry, and other anterior segment parameters, such as anterior chamber depth, angle to angle distances and the like.

Embodiments of the present invention can achieve accurate repeatability since there need be little or no user intervention during an exam. Also, embodiments can include a rotatable touch screen monitor that allows an examination device to be operated from a front side (conventional) or from a patient shoulders, the later of which can be suitable when examining elderly patients that need to adjust their posture or to be helped with opening their eyelids, for example.

BRIEF DESCRIPTION OF THE DRAWINGS

FIG. 2 is a perspective view of select optical elements of a tracking camera system in according to some embodiments of this invention.

FIG. 3 is a perspective view select optical elements of a pair of scheimpflug camera systems according to some embodiments of this invention.

FIG. 4A is a perspective view of select blue light source system components according to some embodiments of this invention.

FIG. 4B is a perspective view of select infra red light source system components according to some embodiments of this invention.

FIGS. 5A-E is an exemplary process for analyzing a patient's eye according to some embodiments of this invention.

DETAILED DESCRIPTION OF THE PREFERRED EMBODIMENT

In the following description of preferred embodiments, reference is made to the accompanying drawings which form a part hereof, and in which it is shown by way of illustration specific embodiments in which the invention may be practiced. It is to be understood that other embodiments may be utilized and structural changes may be made without departing from the scope of the preferred embodiments of the present invention.

Figure 1A:
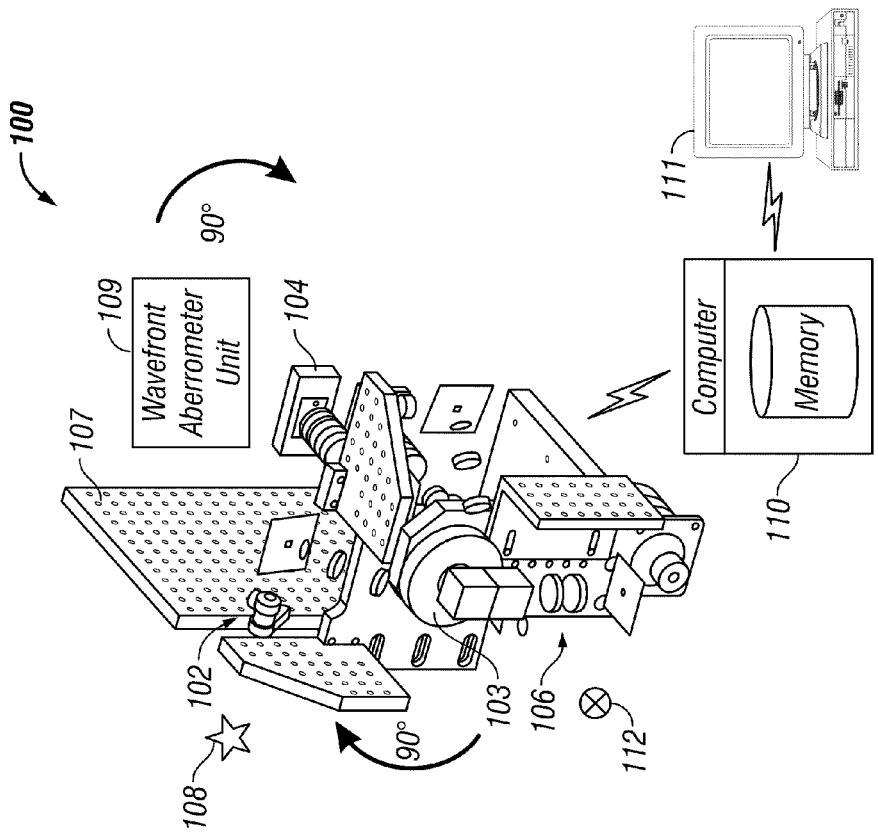
FIG. 1A is a perspective, broken away view of select elements of an exemplary ophthalmologic analyzer device, including various components schematically drawn, according to some embodiments of this invention.
Figure 1B:
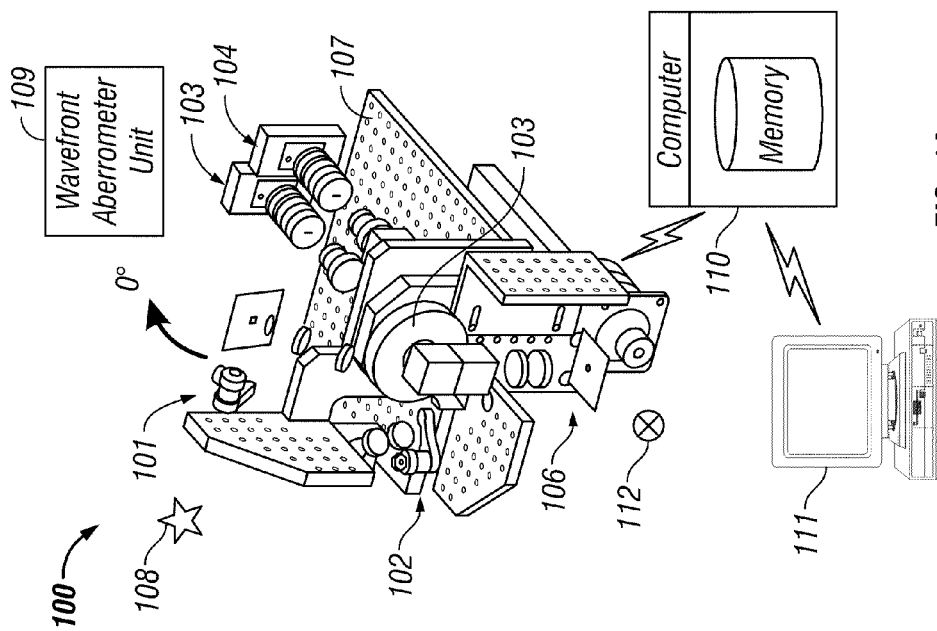
FIG. 1B illustrates the device of FIG. 1A with scheimpflug cameras rotated 90 degrees according to some embodiments of this invention.

With reference to the figures, FIGS. 1A and 1B illustrate an exemplary embodiment of anterior segment analyzer device 100. Device 100 can provide a professional with a complete set of biometric data used to determine geometrical and material parameters of an intraocular lens to be implanted into a patient's eye. Accordingly, this biometric data can be used to custom design a lens that corrects viewing defects of an eye.

FIGS. 1A and 1B illustrate an interior of device 100. Device 100 can include movable platform 107 that can be rotated in a stepless fashion via primary rotor 103. Platform 107 can support two Scheimpflug cameras 101 and 102 and a projection system having two light source systems 103 and 104.

With further reference to FIGS. 1A and 1B, tracking camera system 106 can monitor or detect movements of an eye during an eye imaging session and transmit eye movement information to computer 110. In some embodiments, tracking camera 106 need not be connected to rotatable platform 107, so that when rotatable platform 107 moves, tracking camera 106 can remain in place.

FIG. 2 illustrates optical components of camera tracking system 106 in accordance with some embodiments. The exemplary camera tracking system 106 can include a beam splitter for reflecting light, such as infra-red light, reflected from the eye through an optical projection lens system and onto a CMOS detector.

In response, computer 110 can control tracking rotor 112 (tracking rotor is symbolically depicted in FIGS. 1A and 1B for ease of understanding) in a manner that moves platform 107 and, in turn, Scheimpfulg cameras 101 and 102 in accordance with the detected movements of the eye. In this manner, device 100 can track movements of an eye during an eye imaging session and adjust imaging components, such as Scheimpflug cameras 101 and 102, in accordance with any eye movement so as to maintain proper alignment of the device 100 with the eye. Scheimpflug cameras 101 and 102 can be positioned on rotatable platform 107 at a 90 degree angle with respect to one another.

FIG. 3 illustrates select optical components of Schiempflug cameras 101 and 102 in accordance with some embodiments. Here, each Schiempflug optical system 101 and 102 is configured to satisfy the Scheimpflug principle. To this end, each Scheimpflug camera system is arranged so that an eye plane (e.g., the plane of a patient's eye), a plane of the lens system of the Scheimpflug camera system and a plane of the CCD are inclined with respect to one another in such a way that they intersect in one common axis.

With further reference to FIGS. 1A and 1B, platform 107 can rotate so as to capture various measurements of an eye. FIG. 1B shows rotatable platform 107, and associated components such as cameras 101 and 102, rotated 90 degrees from the position of platform 107 shown in FIG. 1A. In some embodiments, platform 107 can rotate 90 degrees, as a 90 degree rotation can be enough to complete the imaging of an entire cornea and entire anterior chamber of an eye. Device 100 need not be limited to a 90 degree rotation, however, as other embodiments can permit platform 107 to rotate more or less than 90 degrees.

Referring to FIGS. 1A and 1B, projection system can include two light source systems 013 and 104. Light system 104 can have a blue light source and light system 103 can include an infrared light source. Infrared light system 105 can be used to direct infrared light into inner parts of an eye. Infrared light that is reflected back from the eye can then be detected by tracking camera system 106. In some embodiments, tracking camera system 106 can continuously detect the reflected infrared light and transmit a video signal generated from the tracking camera to computer 110 during most or all of an eye imaging session. Blue light system 104 can direct light into the cornea, the lens, and most or the entire anterior chamber of an eye. Light reflected back from the eye can then be captured via Scheimpflug cameras 101 and 102, as Scheimpflug cameras 101 and 102 rotate 90 degrees. In this manner, Scheimpflug cameras 101 and 102 can image the blue light scattered from the outer and the inner surfaces of the cornea, the lens and most of or the entire anterior chamber of an eye.

Figure 1C:
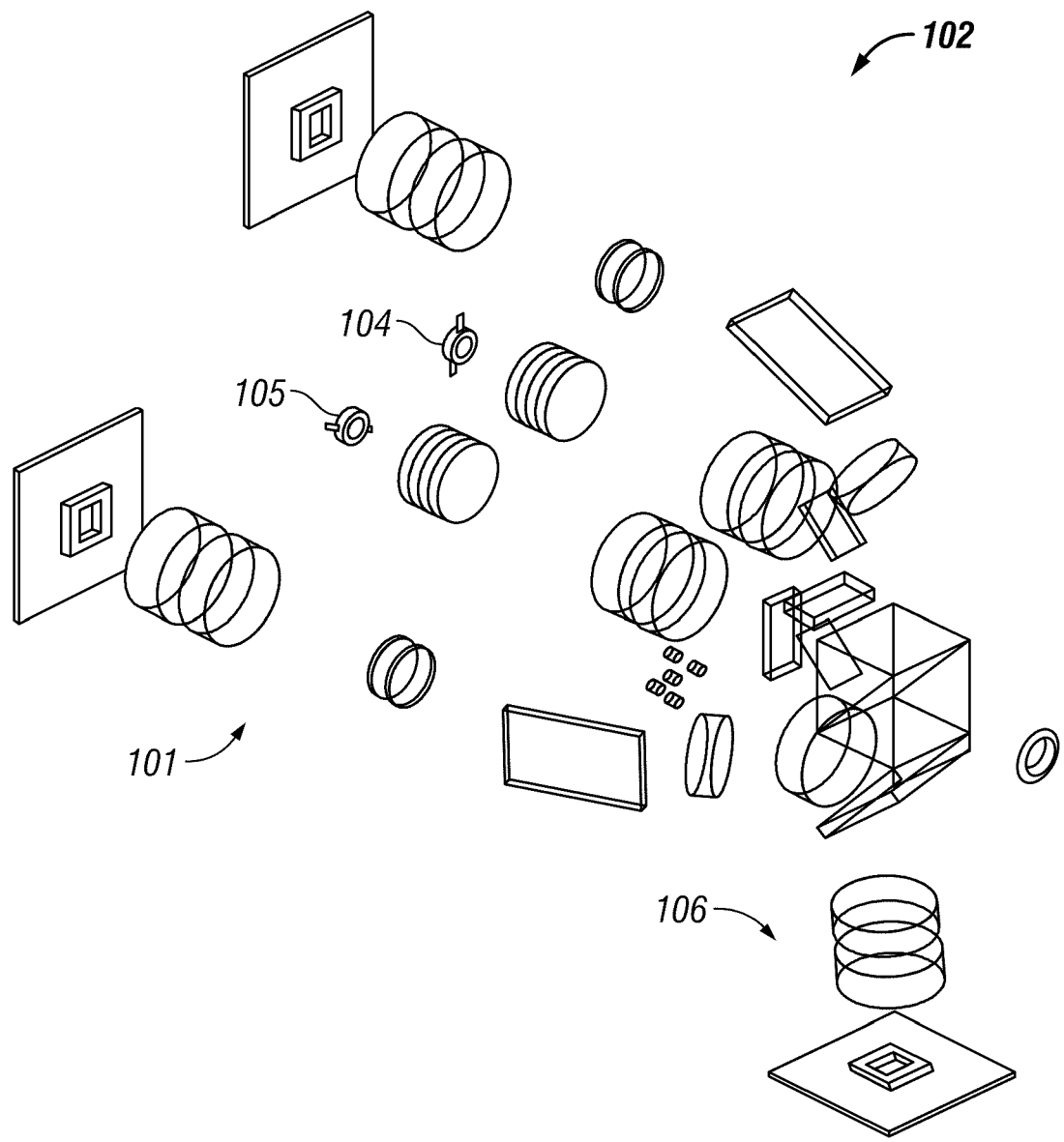
FIG. 1C is a perspective view of select optical elements of an exemplary anterior segment analyzer device according to some embodiments of this invention.

FIG. 1C illustrates select optical components of device 100, such as Scheimpflug cameras 101 and 102, light sources 104 and 105 and tracking cameras 106, in accordance with some embodiments.

Embodiments of light systems 104 and 105 are further illustrated in FIG. 4A and FIG. 4B, respectively. As illustrated, each light system 104 and 105 can include respective light sources 113 and 114 and respective projection systems 115 and 116. Each light source 113 and 114 can produce a slit beam profile of infrared or blue light, respectively. In accordance with some embodiments, diaphragms can be mounted at an intra-focal position in each projection system for producing a slit profile and focused by projection optics. Infrared and blue light sources can Light Emission Diodes (LEDs), an array of LEDs, Laser diodes, or discharge bulbs, for example. In some embodiments, light sources can be positioned on a plane perpendicular to the optical axis of projection optics. In other embodiments, light sources can be positioned on a plane tilted with respect to the same axis.

With further reference to FIGS. 1A and 1B, device 100 can include indicator 108, which can be maintained at a fixed location, separate from movable platform 107. Indicator 108 can be a red LED, for example, but other indicators can be used as well. For example, in some embodiments, a multi-color illuminated pattern can be used as indicator 108. During an eye examination session using device 100, a patient can be instructed to constantly view (e.g., focus on) indicator 108. Tracking camera system 106 can track any eye movement away from the indicator 108. In response to any detected eye movement away form indicator 108, device 100 can adjust platform 107 in accordance with the detected eye movement so as to maintain proper alignment of Scheimpflug cameras 101 and 102 with the eye. In other words, even if the eye moves away from away indicator 108, computer 110 can detect such movement via tracking camera 106 adjust platform 107 positioning via tracking rotor 112 to compensate for the movement of the eye, thereby maintaining proper alignment with the eye. This computer-aided tracking capability of device 100 can be referred to as "intelligent pointer," and it can realize a concept of intelligent alignment.

In accordance with some embodiments, the tilt of Scheimpflug cameras 101 and 102 with respect to a tangential plane on the vertex of the cornea's outer surface, or with respect to the optical axis of an eye, can be less than 40 degrees. This can allow device 100 to obtain improved depth of field imaging inside the eye as well as improve sharpness and provide deeper images of an eye. Improvement in resolution can also be achieved by combining video data streams from each Scheimpflug camera 101 and 102. Each video stream can be transmitted to computer 110 for processing.

From the video provided from Sheimpflug cameras 101 and 102, computer 110 can process the data and construct a complete cornea topographic profile, a pachimetric profile, a detailed topography of both surfaces of the eye lens, and a set of biometric data relating to the anterior chamber of an eye. This information can be obtained by a 90 degree rotation of the two Scheimpflug cameras 101 and 102, which can be titled at a 90 degree angle from one another while being rotated.

In accordance with some embodiments, a wavefront aberrometer unit 109, which is merely symbolically depicted in FIGS. 1A and 1B, can be optionally included in device 100. Wavefront aberrometer unit 109 can emit one or more predefined wavefronts towards an eye. Each wavefront can be an infrared, mathematically pre-shaped and well known wavefront, for example. Aberrometer unit 109 can also detect and measure each wavefront reflected backward from the eye and, by comparing the two wavefronts, aberrometer unit 109 can provide a professional the information needed to evaluate viewing defects of the eye under examination. An exemplary aberrometer unit be the aberrometer 1300, described in more detail with respect to FIG. 13.

In accordance with some embodiments, device 100 can optionally include design and modeling software, in the form of computer readable instructions, residing in memory of computer 110. Such software can provide instructions to processor of computer 110 to process information obtained from cameras 101 and 102 as well as information inputted into computer 110 via an input device (not shown). The input device can be a keyboard, mouse, trackball or touch sensitive display, for example. The inputted information can include geometrical parameters relating to a shape of surfaces of a manufactured intraocular lens, dimensions of an intraocular lens, and material by which an intraocular lens can be manufactured. Subsequently, the computer 110, using software residing in computer, can provide a professional a complete set of data output explaining a simulated performance of an intraocular lens having the previously inputted parameters when it is installed into an eye.

As briefly described above, device 100 can include a touch sensitive display unit 111. Display unit 111 can provide an interface for operating device in an easy and quick manner. As an example, a professional operating device 100 can access output data on-demand, by positioning a virtual marker displayed on touch screen 111 over areas of a previously acquired image of an anterior chamber of an eye. The professional can then select various measurements on the selected area for analyzing that area. Of course, display unit 111 need not be touch sensitive, as other input devices can be used as well.

As discussed above, device 100 can maintain alignment of an eye along a viewing optical axis so that measurement equipment can obtain and output most or all biometrical parameters needed to design an intraocular lens. Accordingly, device 100 can be described as an anterior eye chamber meter, which can detect and measure minute details of surfaces or volumes of an anterior segment of an eye. In this manner, thickness and surfaces of the cornea, iris, pupil and lens can be fully mapped.

Advantageously, device 100 can also measure linear dimensions of an anterior chamber of an eye filled with the watery humor, a total volume of the anterior chamber, and an amplitude of the angles an inner surface of the cornea forms with an edge surface of the iris. The linear dimensions of the anterior chamber can also be referred to as an angle-to-angle distance, and the angular amplitude can be referred to as an amplitude of the angle.

Data collected during an eye examination session using device 100 can include a corneal profile, both outer and the inner surface topography, altitudes maps and corneal pachimetry. This collection of data can be referred to as a first set of data. From this first set of data, a professional can determine the presence of Keratoconus and, more generally, evaluate any defects of the cornea. The topographic maps can be delivered (e.g., displayed on display 111) to a professional as one or more different colored maps, each color on a map representing a different value (can also be referred to as a zero-quote). Altitude maps can use a different colored map, wherein each color can represent a value (can also referred to as a vertex of the cornea).

A second group of data that can be obtained using device 100 can include angle-to-angle distance, an amplitude of the angle and a total anterior chamber volume. This set of data can be used to evaluate optical aberrations of an eye and other viewing defects of an eye that can be determined by an anterior chamber analysis.

A third group of data can include a distance between the cornea and the lens, a complete mapping of both surfaces of the lens (i.e. the front and the back surface), and settling capabilities of the lens. This group of measures can be used to evaluate overall viewing defects of an eye, as well as to provide a professional with design information and parameters for prescribing an intraocular lens, for example.

A fourth group of output data that can be obtained using device 100 can be densitometry data of the lens, which can allow a professional to produce a densitometry analysis of the lens itself. The fourth data output can also include a set of on-demand measurements ordered by a professional using device 100 relating to additional information about the anterior chamber of an eye. This set of on-demand data can by requested from the professional, who can receive such information by positioning a virtual marker on desired area of a previously acquired image of the frontal chamber of an eye, by the means of touch screen display 111. Depending upon what points on the image a professional selects, device 100 can provide various types of information, such as thickness data, distance data or the like, related to the selected area.

Optionally, a fifth group of data can also be obtained using device 1000, the fifth group of data can be related to use of optional aberrometer unit 109. This group of data can be include interferometric measurements comparing a wavefront emitted by the unit 109 to the resulting wavefront reflected backward from the inner parts of the anterior chamber of an eye, for example. Computer 110 can process the wavefront measurement and provide output data useful for designing a corrective intraocular lens.

A sixth group of output data can also be obtained from device 100. As discussed above, specifications relating to an intraocular lens, such as its surface, thickness and material data, can be inputted into device 100. This data can be used to simulate the optical performance of the intraocular lens as if it were positioned inside the lens chamber into an eye. Thus, this simulation can be performed prior to an intraocular lens having those specifications is implanted into an eye. In other words, device 100 can simulate the optical performance of an existing but not already implanted intraocular lens. Thus, device 100 can provide a professional with a means to realize whether a candidate intraocular lens will properly perform correct viewing defects of an eye once implanted.

Figure 5A:
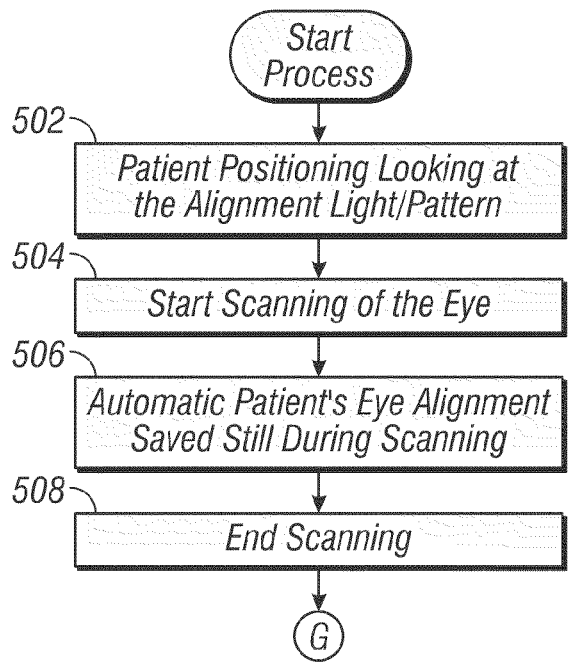
Figure 5B:
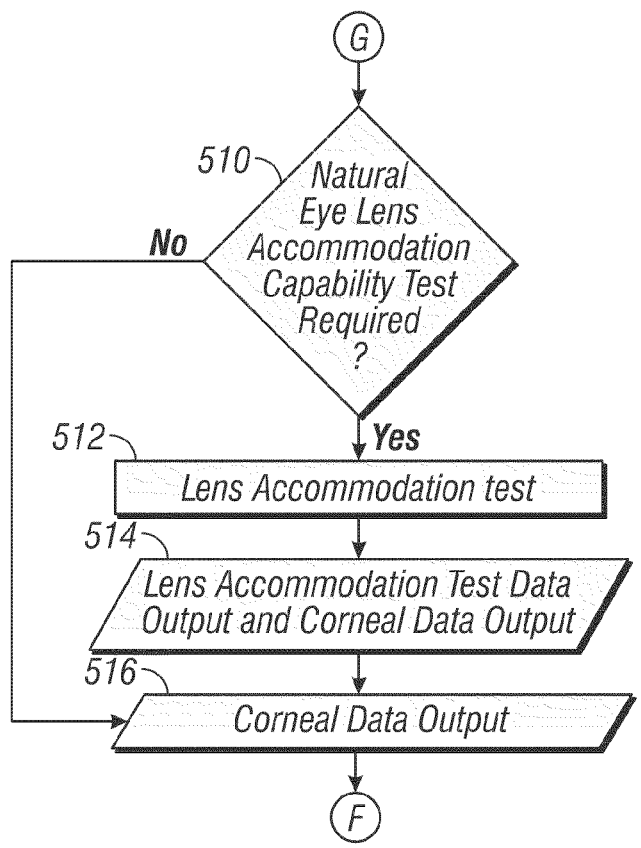

Exemplary process 500 for obtaining measurements of an eye in accordance with some embodiments is described with reference to FIG. 5. Many of the steps described in process 500 can be automatically performed computer-readable instructions residing in memory of device 100, for example. In addition, one skilled in the art will appreciate that various timing and memory storage issues are omitted from this flowchart for the sake of clarity.

Process 500 can begin at step 502, where a patient is positioned with device 100 so that the patient is looking at indicator 108. Scanning can then begin in step 504. Scanning can include rotating both Scheimpflung cameras 101 and 102 in a 90 degree arc, all the while providing video output from cameras 101 and 102 to computer 110. Furthermore, in step 506, device 100 can detect any eye movement during scanning step 504. If movement is detected, then device 100 can adjust cameras 101 and 102 in accordance with the eye movement. After a full 90 degree rotation, scanning can be complete in step 508.

Device 100 can also query whether a natural lens accommodation capability test should be performed in step 510. If a lens accommodation test need not be performed, then process 500 can proceed to step 516 where corneal data obtained in previous steps can be stored in device 100 for later processing. On the other hand, if a lens accommodation test should be performed, then device 100 can automatically perform a lens accommodation test in step 512. Data obtained during step 512 can then be stored in device 100 in step 514 for later processing.

Next, in step 518, device 100 can query whether complete anterior chamber data is needed. If yes, then anterior chamber data can be stored in step 520. After step 520 or if the answer is no in step 518, process 500 proceeds to step 522. In step 522, device 100 can query whether biometric intraocular lens specifications and design is requested. If no, then process 500 can proceed can end at step 530. On the other hand, if yes, then device 100 can provide intraocular lens specification and design data in step 524. Process can then query for correction data to be inputted in step 526. If no data correction is to be inputted, then process 500 can end at step 530. If lens design corrections are to be inputted, then such corrective data can be inputted and process 500 can proceed to step 528. In step 528, modified intraocular lens specifications design data can be outputted. Process can then end at step 530.

One or more steps of process 500 can be performed by instructions in the form of computer-readable residing in memory of computer 110. Note that instructions can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any medium that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM) (magnetic), an optical fiber (optical), portable optical disc such a CD, CD-R, CD-RW, DVD, DVD-R, or DVD-RW, or flash memory such as compact flash cards, secured digital cards, USB memory devices, memory stick, etc. Note that the computer-readable medium could even be paper or another suitable medium upon which the program is printed, as the program text can be electronically captured via optical scanning of the paper or other medium, then compiled, interpreted or otherwise processed in a suitable manner if necessary, and then stored in a computer memory In accordance with some embodiments, device 100 can include a housing containing various components of the device.

Figure 6:
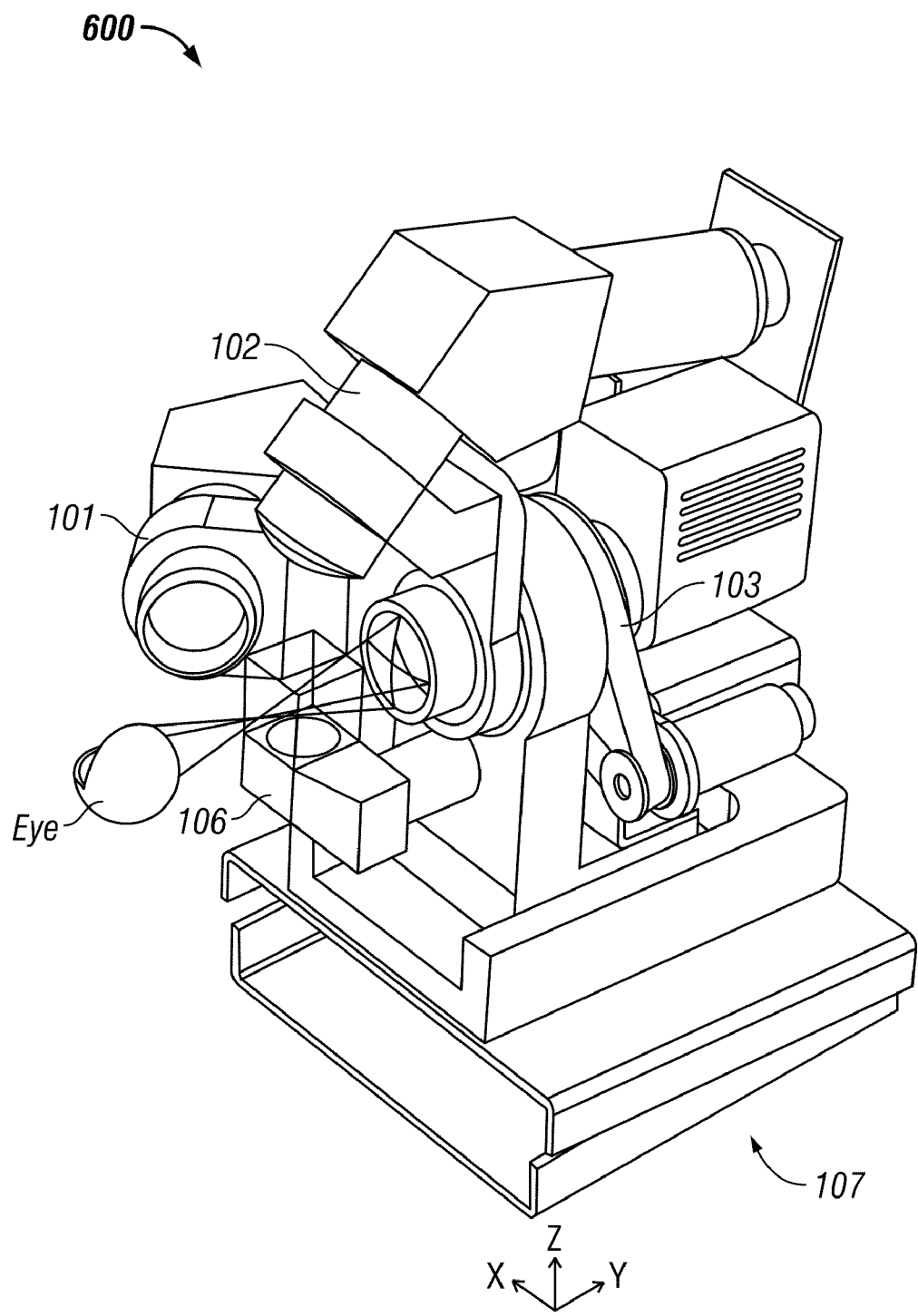
FIG. 6 is perspective view of an exemplary implementation of exemplary ophthalmologic analyzer device according to some embodiments of this invention.

An exemplary embodiment 600 is illustrated in FIG. 6. As illustrated, Scheimpflug cameras 101 and 102 are positioned at about a 90 degree angle from one another. Platform 107 can move in the x, y and z directions, as well as tilt, so as to maintain alignment of the cameras with a patient's eye and compensate for eye movement of the eye. To this end, tracking camera 106 is positioned and configured to track any movement of the eye. In operation, rotor 103 can rotate cameras 101 and 102 approximately 90 degrees for obtaining measurements of the eye.

Figure 7A:
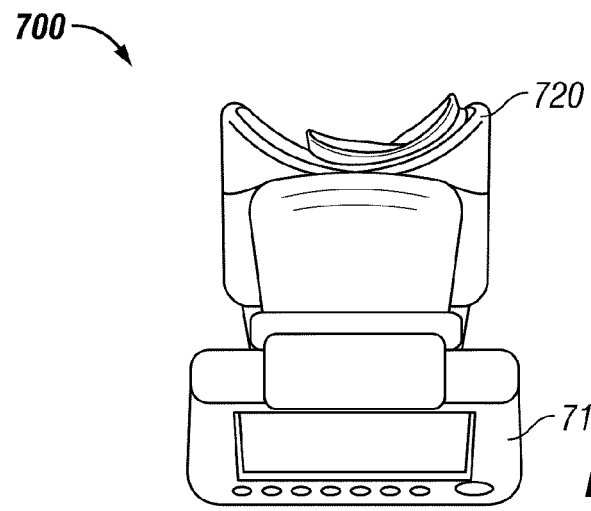
FIGS. 7A, 7B and 7C are respective top, perspective and side views of another exemplary ophthalmologic analyzer device according to some embodiments of this invention.
Figure 7B:
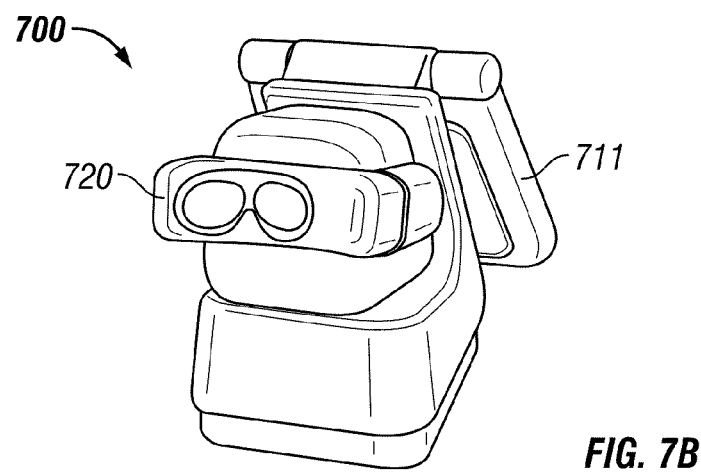
Figure 7C:
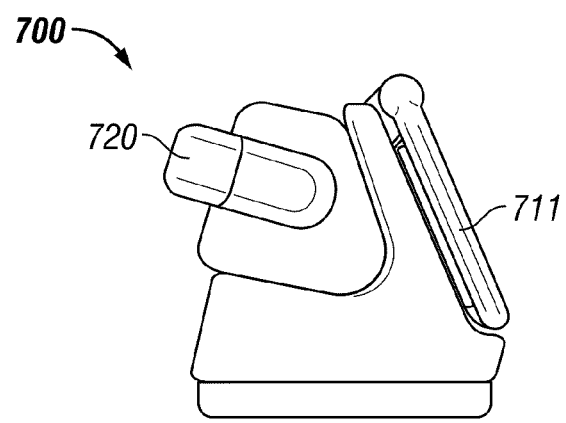

Top, perspective and side views of a further exemplary embodiment are illustrated in respective FIGS. 7A, 7B and 7C. Device 700 can contain the various components of device 100 described above in a compact housing. In addition, device 700 can include a headrest 720, which can aid in positioning a patient in front of device 700. Device 700 can also include touch-sensitive display panel 711, similar to display 111 described with reference to FIG. 1A. Conveniently, Scheimpflug cameras 101 and 102 can reside inside and rotate inside housing of device 700 during an eye examination.

An exemplary embodiment of anterior segment analyzer (ASA) device 800 and methods of using the same will now be described with reference to FIGS. 8-21. It should be understood that various components and process described with reference to FIGS. 8-21 can be identical or similar to components and process described above with reference to FIGS. 1-7.

Figure 8:
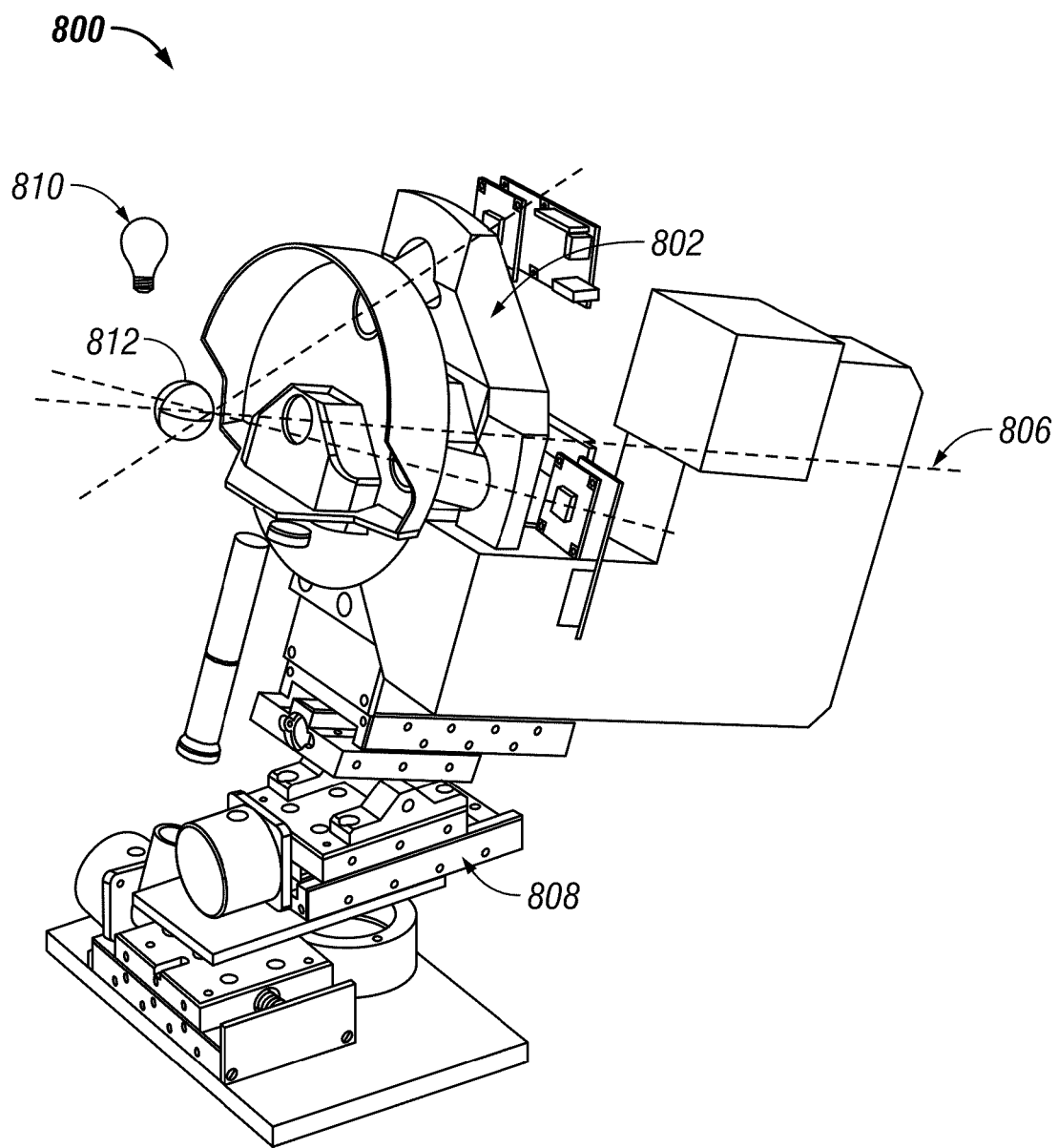
FIG. 8 is a partially broken away view of an exemplary anterior segment analyzer device according to some embodiments of this invention.

FIG. 8 illustrates ASA 800 with various components taken away to illustrate certain features. ASA 800 comprises a rotating Scheimpflug system 802 mounted on a rotating platform 804. In one embodiment, the Scheimpflug system 802 is capable of rotating 90 degrees about optical axis 806. An optical head can be supported by a three-axis mechanical assembly 808 that is driven by an electronic board (for example electric board 1604 illustrated in FIG. 16) and connected to and controlled by an internal computer (for example computer 1602 illustrated in FIG. 16) that can automatically align examined eye 812 with the ASA 800. ASA device 800 can also include an infra-red (IR) light emitting diode (LED) 810 positioned to illuminate a front part of examined eye 812. In this manner, a pupil camera system (for example pupil camera system 1000 described in more detail in FIG. 10) can capture images of the eye pupil of examined eye 812 and maintain alignment of the optical axis 806 with the visual axis of the examined eye 812.

Figure 9:
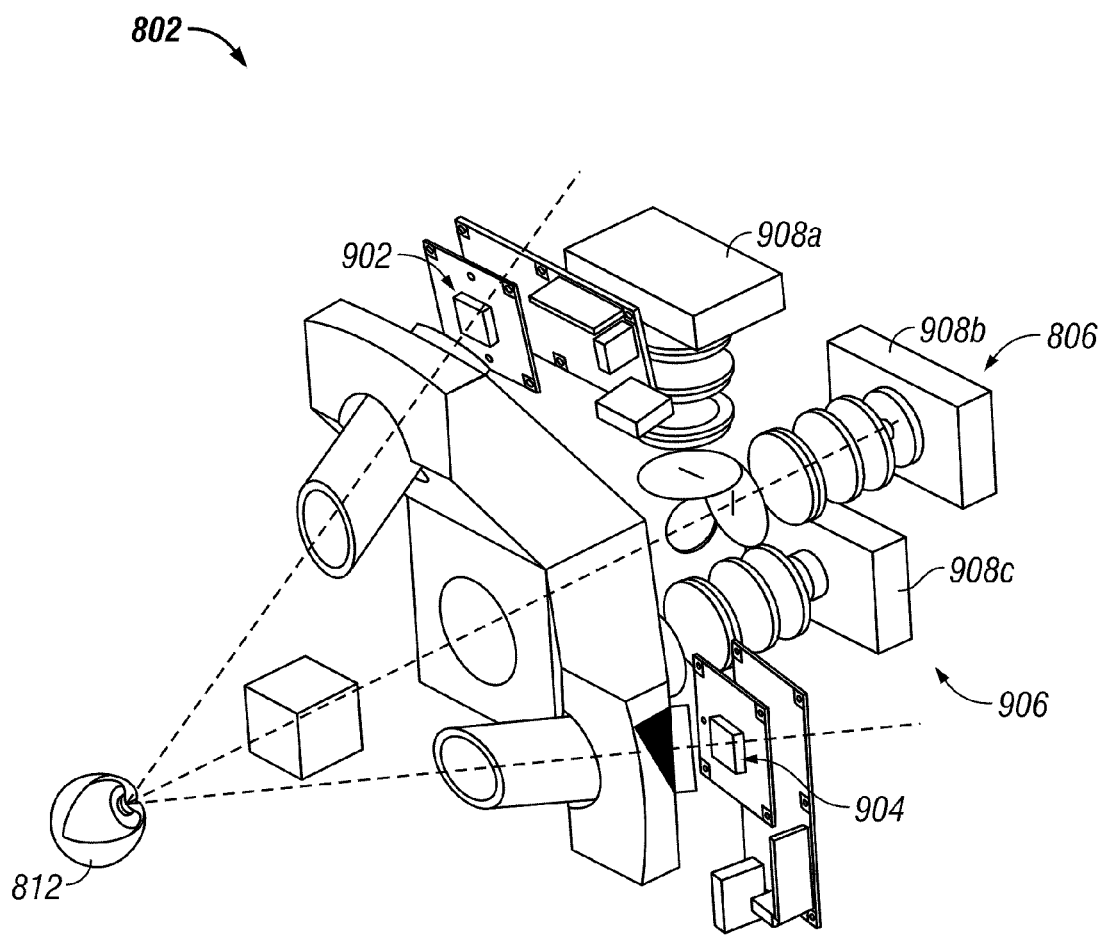
FIG. 9 illustrates various optical systems of the anterior segment analyzer device of FIG. 8 according to some embodiments of this invention.

FIG. 9 illustrates optical components of Scheimpflug system 802 in accordance with one embodiment. Scheimpflug system 802 can comprise a first camera 902 and a second camera 904. FIG. 9 also illustrates light projection system 906 configured and operable to project light emitted from light sources 908a, 908b and 908c toward examined eye 812. The light sources 908a, 908b and 908c can comprise a combination of IR and blue LEDs. FIG. 9 also illustrates optical axis 806 of ASA 800 aligned with a visual axis of examined eye 812.

Figure 10:
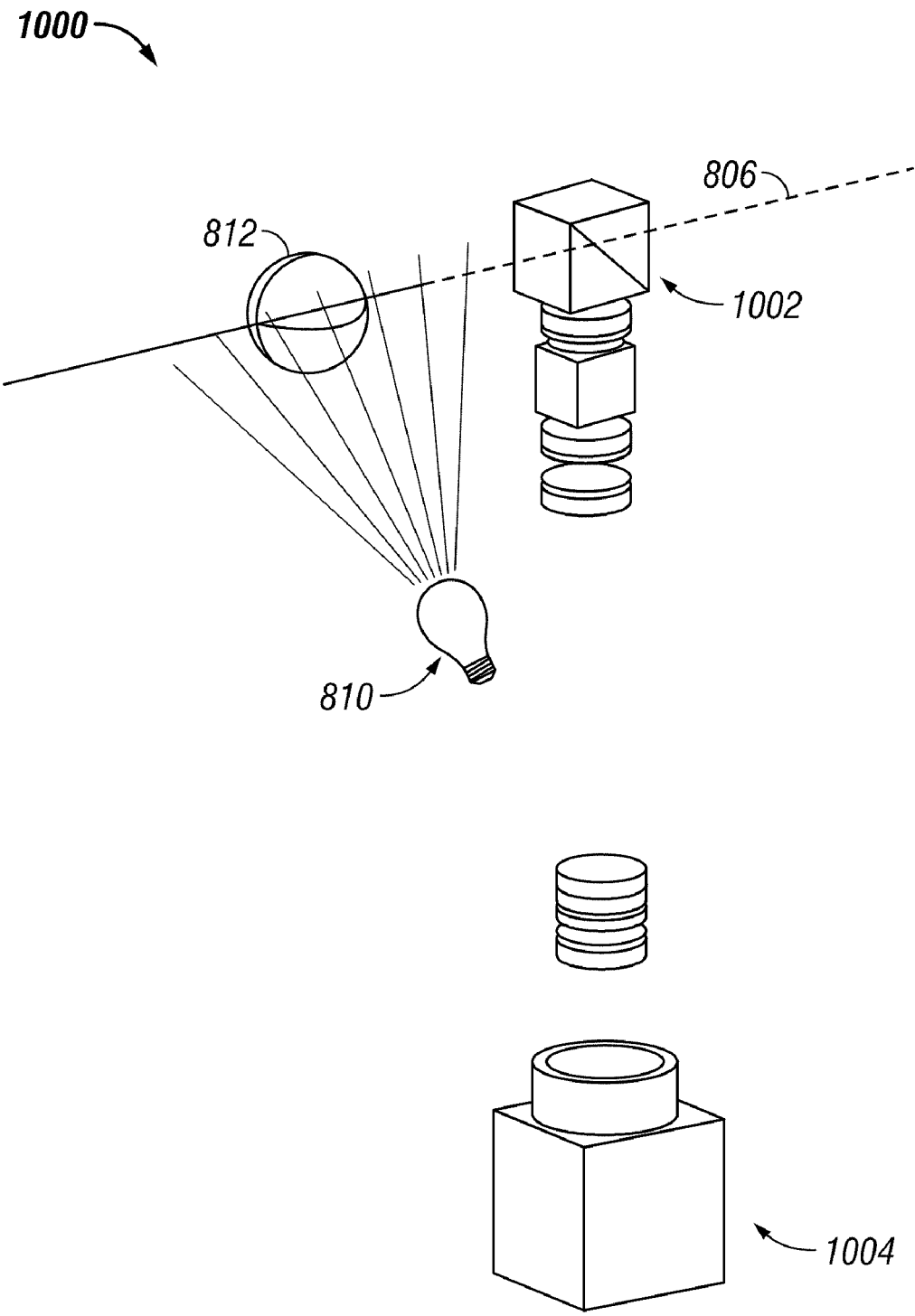
FIG. 10 illustrates an exemplary pupil camera system that may be incorporated in the anterior segment analyzer device of FIG. 8 according to some embodiments of this invention.

FIG. 10 illustrates optical components of pupil camera system 1000 in accordance with one embodiment. Pupil camera system 1000 can include a prism beam splitter 1002 configured to split light propagating along optical axis 1002 from examined eye 812 toward pupil camera 1004. Pupil camera system 1000 also includes IR LED 810 configured to illuminate the iris and pupil of examined eye 812 so that pupil camera 1004 can capture images that are analyzed by internal computer system (for example computer 1602 of FIG. 16).

Figure 11:
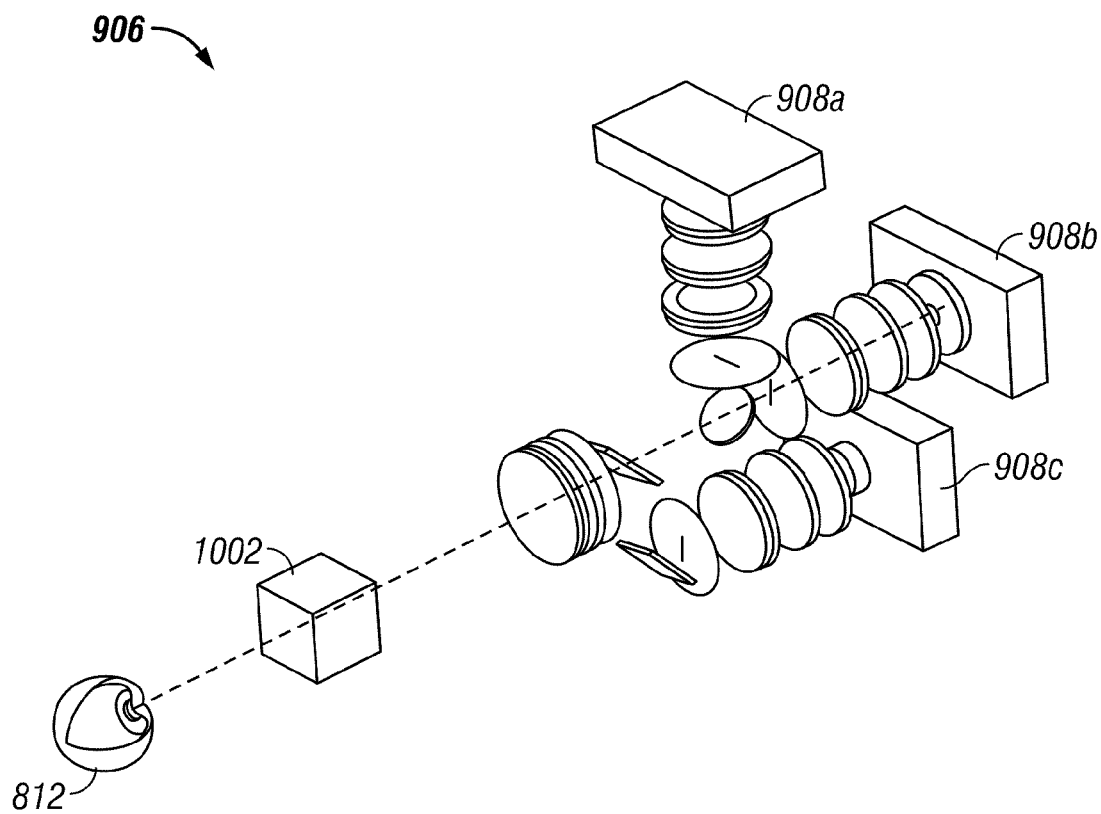
FIG. 11 illustrates an exemplary light projection system that may be incorporated in the anterior segment analyzer device of FIG. 8 according to some embodiments of this invention.

FIG. 11 illustrates light projection system 906 in accordance with one embodiment. In one embodiment, light sources 908a and 908b are blue light emitting LEDs and light source 908c is an IR light emitting LED.

Figure 12:
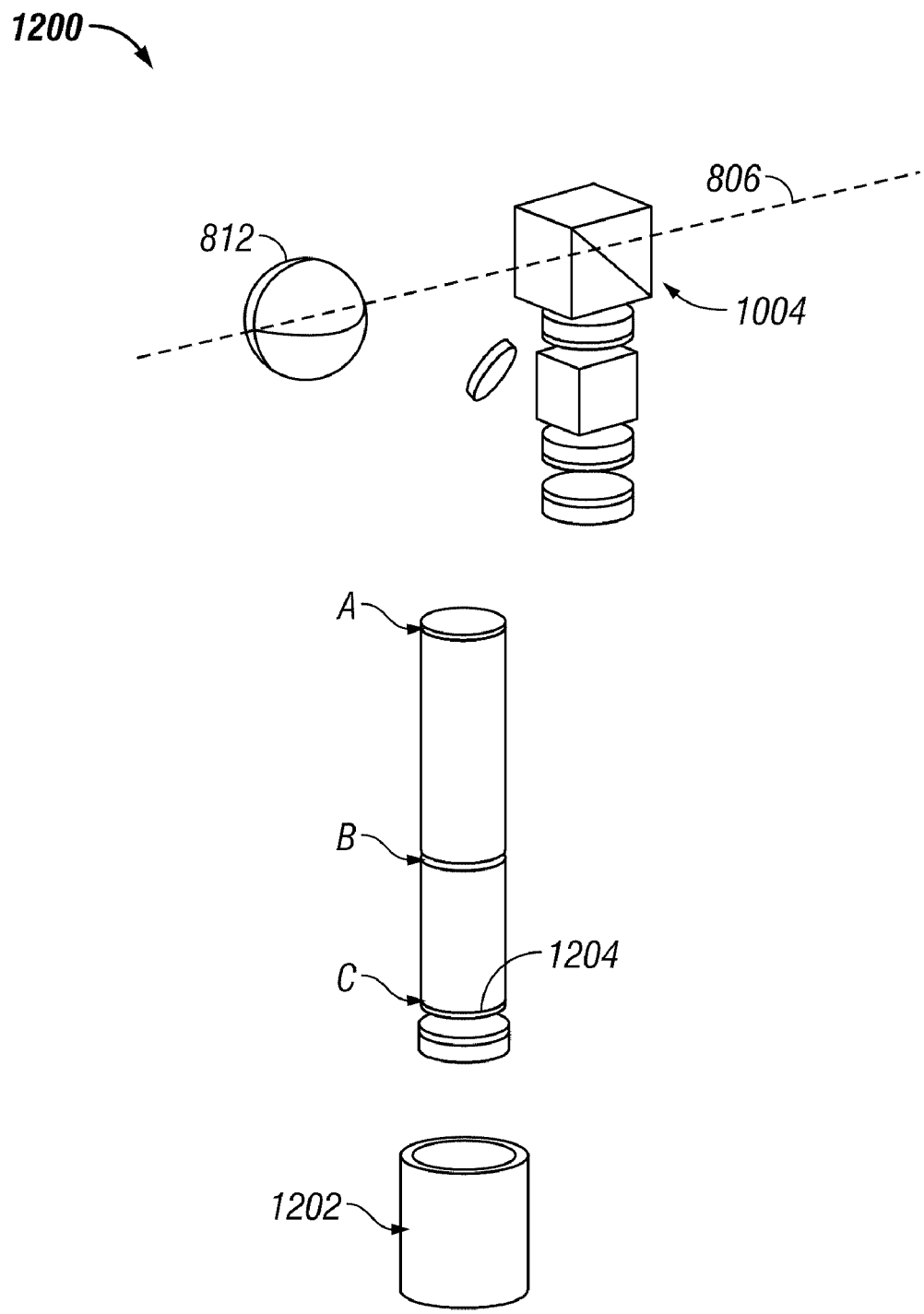
FIG. 12 illustrates an exemplary target fixation system that may be incorporated in the anterior segment analyzer device of FIG. 8 according to some embodiments of this invention.

FIG. 12 illustrates a fixation target system 1200 in accordance with one embodiment. Fixation target system 1200 can share prism beam splitter 1004 merges/splits pupil camera system 1000 (FIG. 10) optical axis 806. Fixation target system 1200 can include fixation target 1202 formed of a pattern of LED or colored, back illuminated pictures, that are projected into the focal plane of the examined eye 812 retina by means of focusing lens 1204. FIG. 12 illustrates that focusing lens can be moved between various positions, such as a far focusing position A, a near focusing position B or any position between far and near positions A and B, respectively, like, for example, an intermediate focusing position C.

Figure 13:
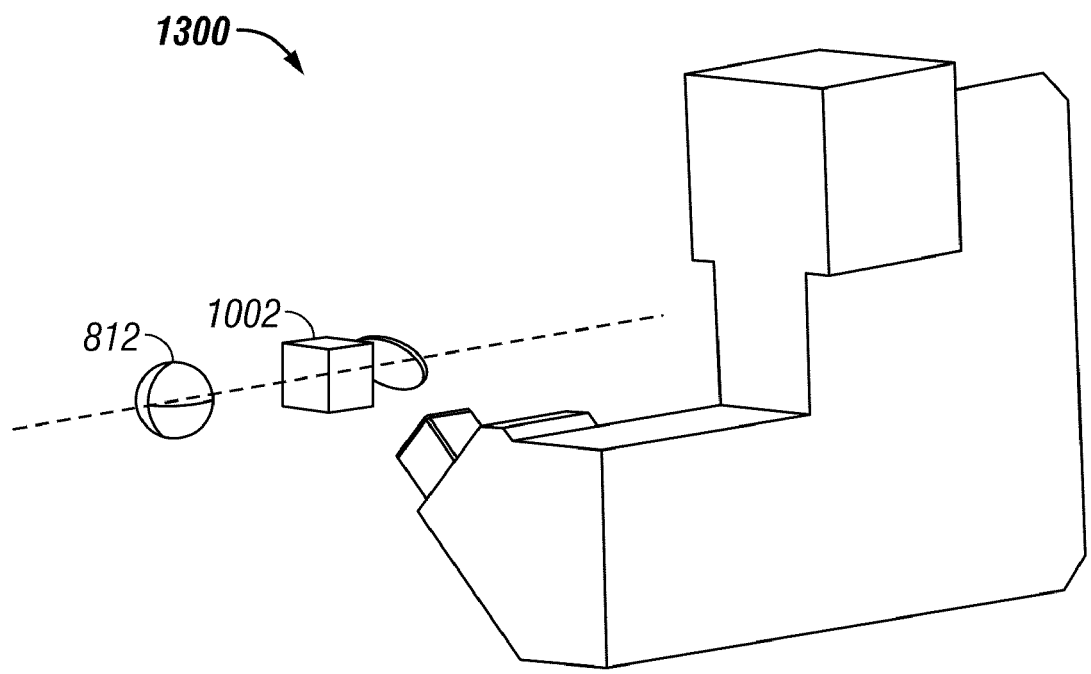
FIG. 13 illustrates an exemplary wavefront sensing system that may be incorporated in the anterior segment analyzer device of FIG. 8 according to some embodiments of this invention.

FIG. 13 illustrates a wavefront sensing system 1300 that can be incorporated in ASA device 800 in accordance with one embodiment. In general, wavefront sensing system 1300 can emit wavefronts and measure wavefronts reflected from and examined eye. Wavefront sensing system 1300 can include a laser projection system (not shown) that projects a light stimuli into the focal plane of the examined eye retina. Wavefront sensing system 1300 also incorporates a wavefront sensor (not shown) operable to receive and detect wavefronts reflected from the examined eye 812.

Figure 14:
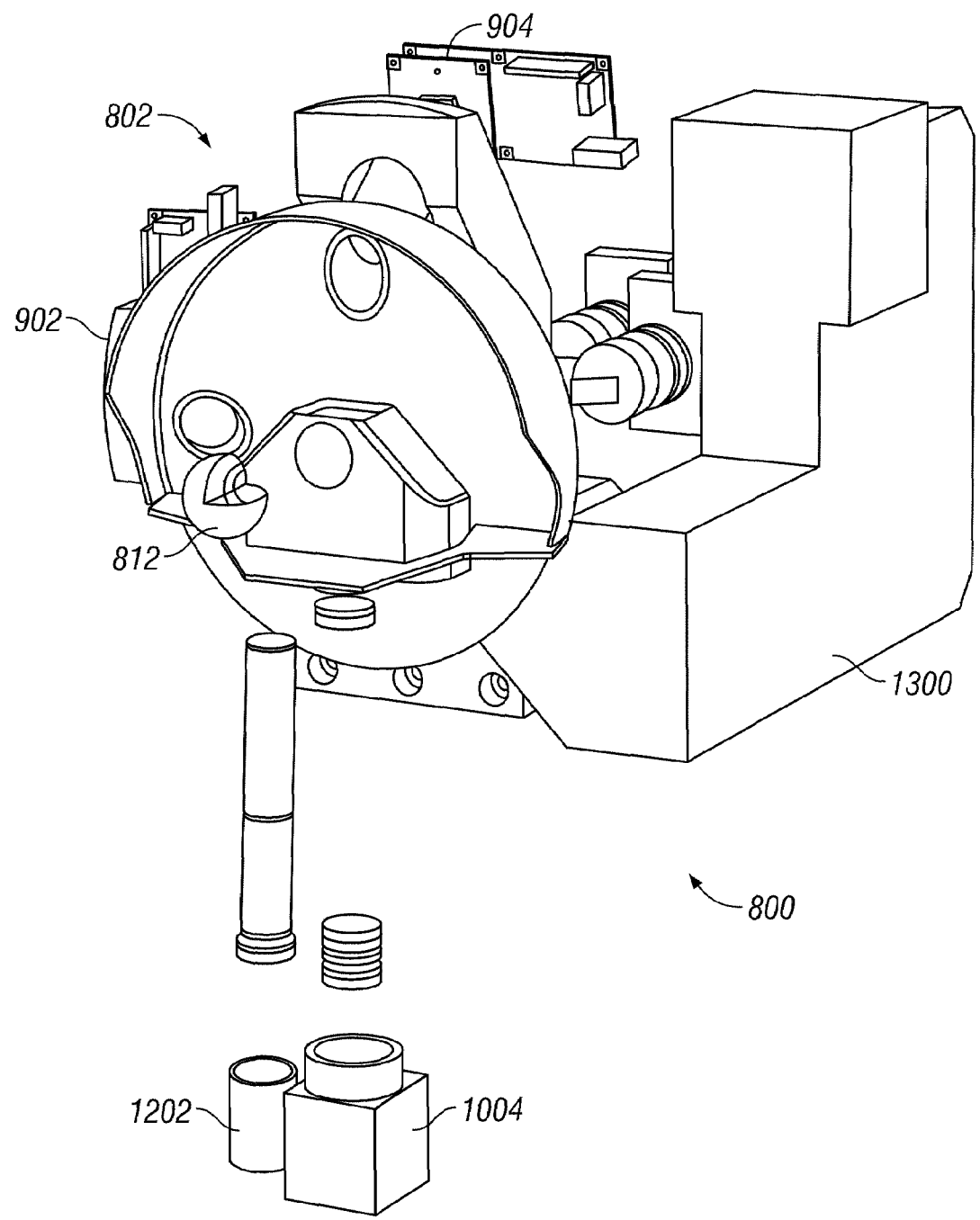
FIG. 14 illustrates an exemplary optical platform that may be incorporated in the anterior segment analyzer device of FIG. 8 according to some embodiments of this invention.

FIG. 14 is a perspective view of ASA device 800 with various components broken away (including mounting mechanical assembly 808) for ease of understanding. It can also be noted that FIG. 14 illustrates cameras 902 and 904 of Scheimpflug system 802 are rotated 90 degrees with respect to the optical axis 806 compared to the position of the cameras 902 and 904 illustrated in FIG. 8.

Figure 15A:
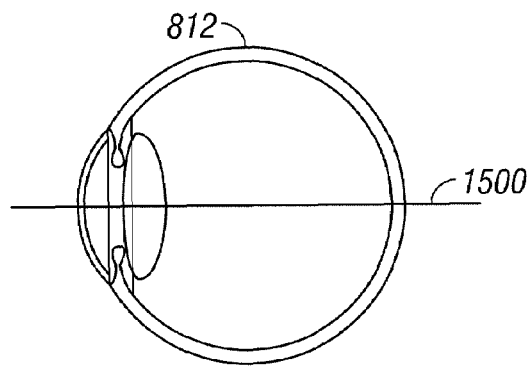
FIGS. 15A-15D illustrate various axes of a human eye.
Figure 15B:
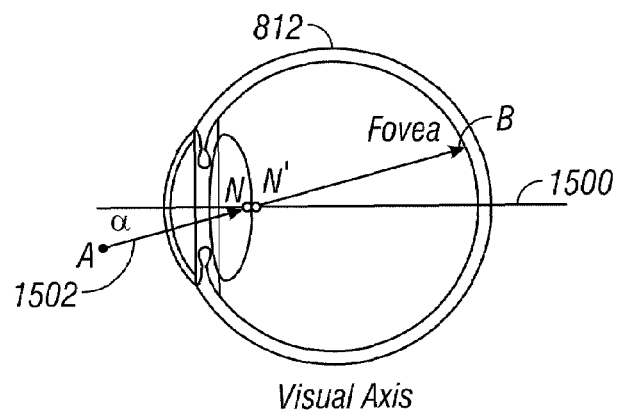
Figure 15C:
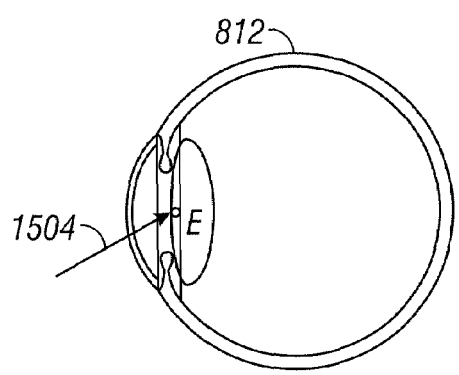
Figure 15D:
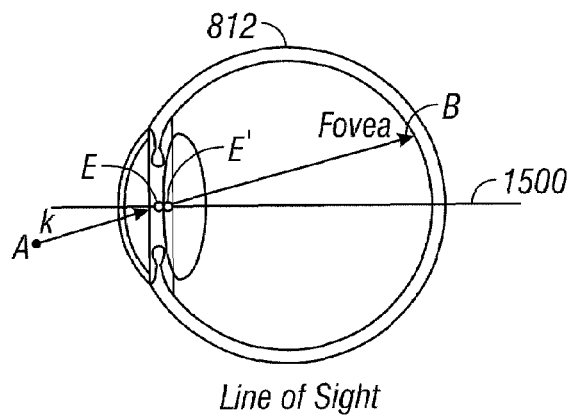

In order to understand the proper eye alignment and the benefits of a proper alignment during the eye examination, a brief explanation of the eye axes are described with reference to FIGS. 15A-15D. With reference to FIG. 15A, a line passing through the center of curvature of the optical surfaces of an eye 812 in a least squares sense can be referred to as an optical axis of the eye 1500. In general, optical axis 1500 can in some instances be ill-defined due to complex shapes of the various ocular surfaces. With reference to FIG. 15B, a visual axis 1502 can be defined herein as connecting a fixation point A to a front nodal N and a rear nodal N' to a fovea B. Visual axis 1502 can deviate from optical axis 1500 by an angle α measured from optical axis. Typically, $4° \leq \alpha \leq 8°$. With reference to FIG. 15, a papillary axis 1504 can be defined herein as an axis that strikes the cornea of eye 812 at a right angle and passes through the center of the entrance of the pupil of the eye 812. With reference to FIG. 15D, a line of sight (LOS) axis can be defined herein as an axis connecting a fixation point A to a center of the entrance pupil E of the eye 812 and the center of the exit pupil E' to the fovea B. The LOS can be equivalent to the chief ray from the fixation point A. The LOS, with angle K from pupillary axis 1504 typically has the following relationship: K≦α.

Figure 16:
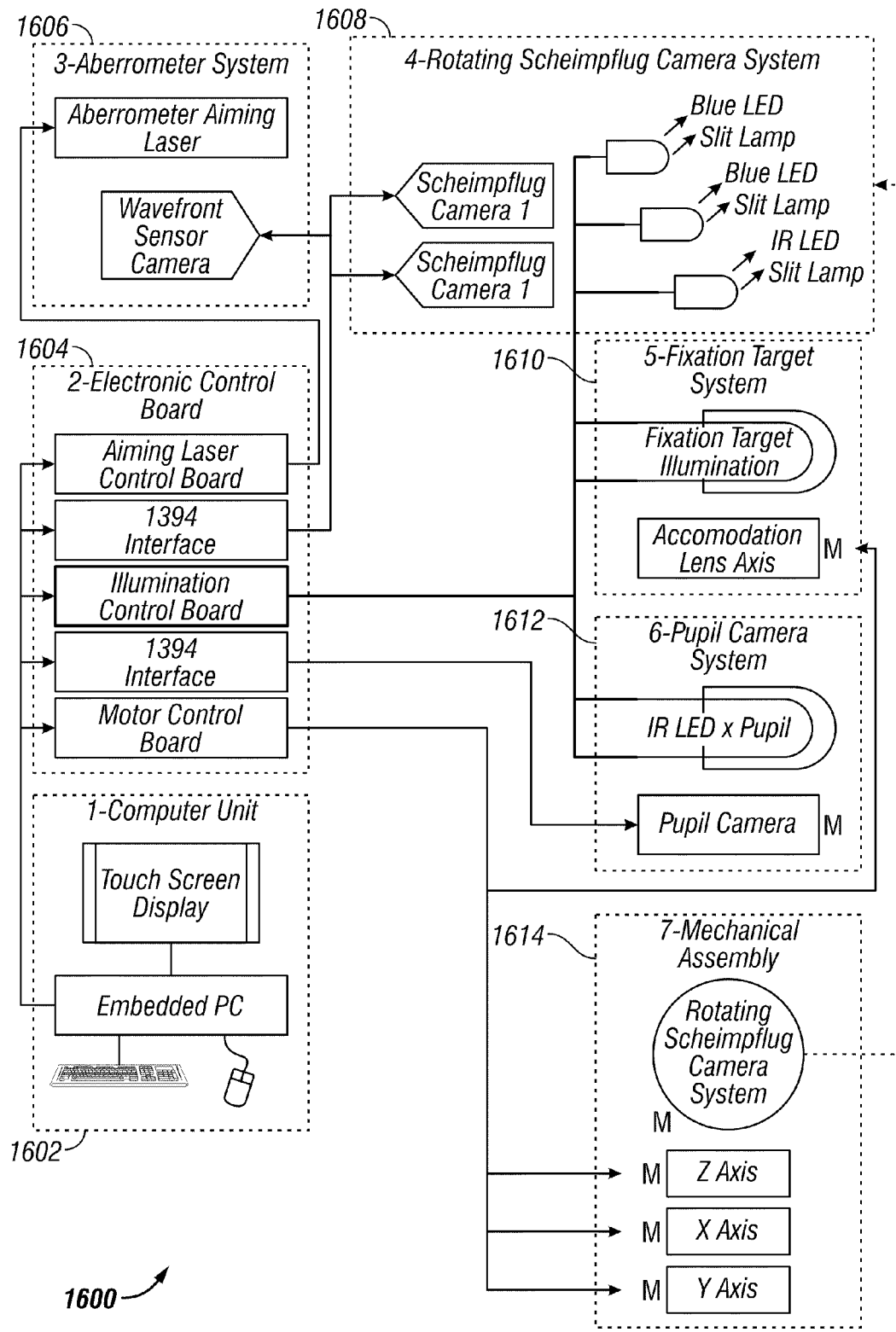
FIG. 16 is a schematic diagram of an exemplary anterior segment analyzer system according to some embodiments of this invention.

FIG. 16 is a schematic diagram of an exemplary ASA system 1600 in accordance with one embodiment. Various components of ASA system 1600 can be identical or similar to the ASA device 800 described with reference to FIGS. 8-15. ASA system 1600 comprises computer unit 1602, electronic control board 1604, aberrometer system 1606, rotating Scheimpflug camera system 1608, fixation target system 1610, pupil camera system 1612 and mechanical assembly 1614.

Figure 17A:
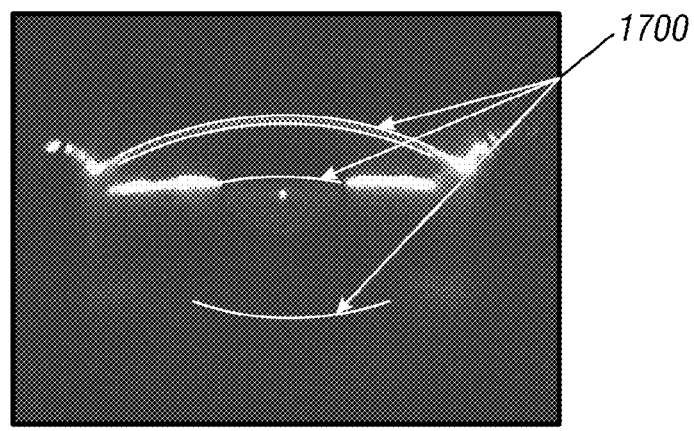
FIGS. 17A-17C are exemplary Scheimpflug and pupil images.
Figure 17B:
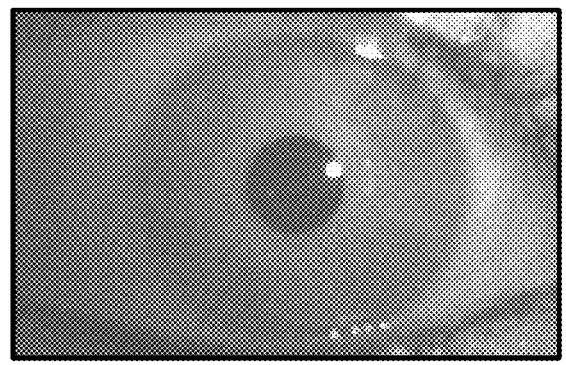
Figure 17C:
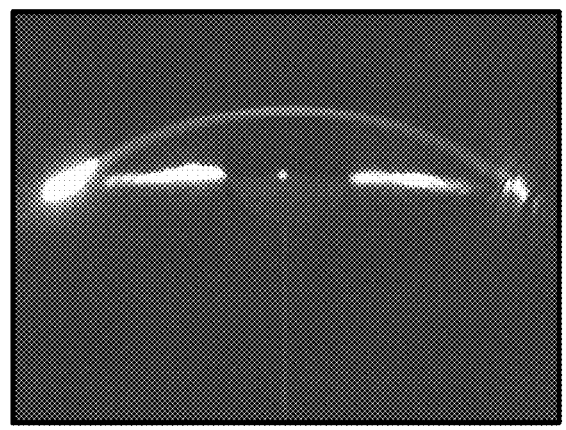

FIGS. 17A and 17C are exemplary scheimpflug images taken by Scheimpflug cameras, such as cameras 902 and 904 of FIG. 9. FIG. 17B is an exemplary image taken by a pupil camera, such as pupil camera 1004 of FIG. 10. FIG. 17A additional depicts enhanced extracted profiles 1700 of the illustrated scheimpflug image.

Figure 18:
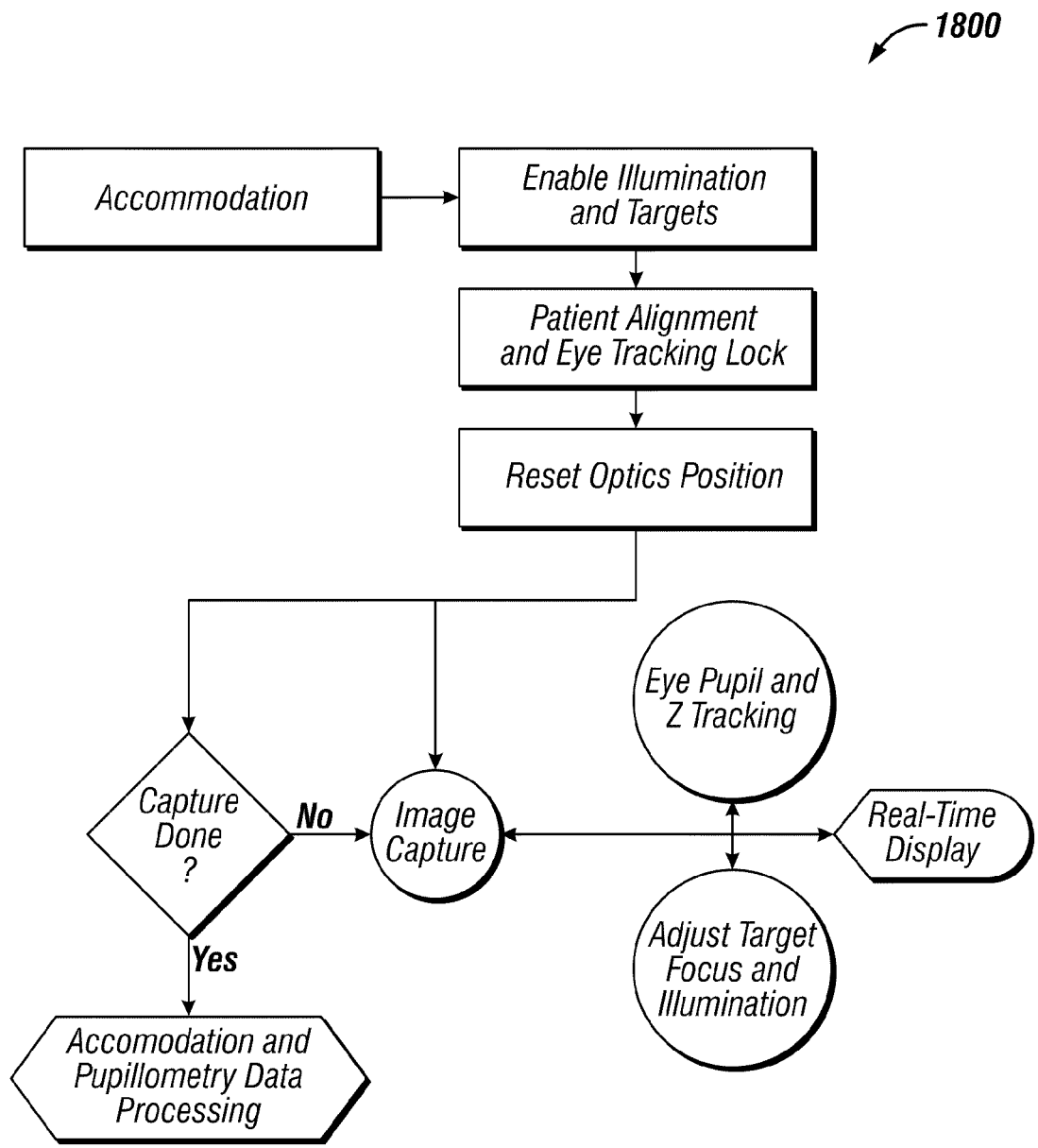
FIG. 18 is an exemplary flow diagram of an accommodation examination according to some embodiments of this invention.

FIG. 18 is an exemplary flow diagram an accommodation examination process 1800 in accordance with one embodiment. The various tasks performed in connection with process 1800 may be performed by hardware, software, firmware, or any combination thereof. It should be appreciated that process 1800 may include any number of additional or alternative tasks. The tasks shown in FIG. 18 need not be performed in the illustrated order, and process 1800 may be incorporated into a more comprehensive procedure or process having additional functionality not described in detail herein.

Figure 19A:
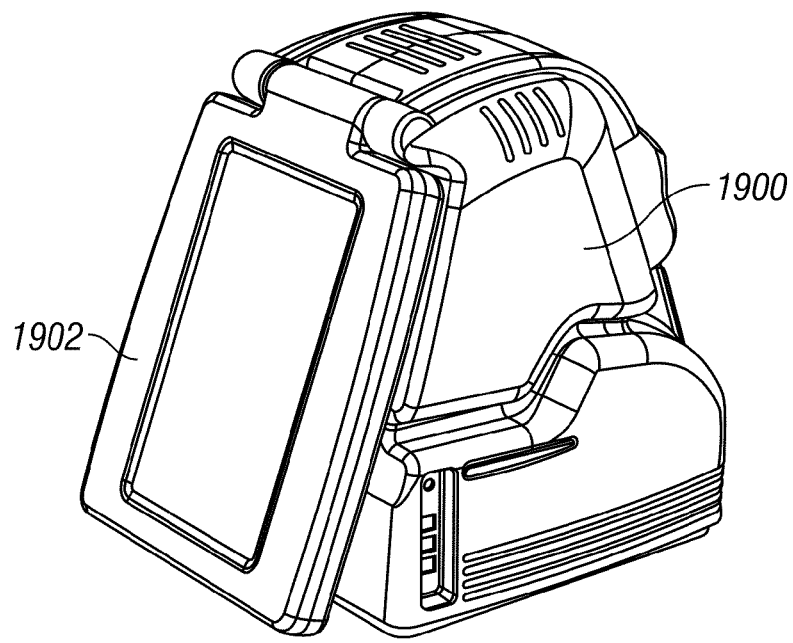
FIGS. 19A-19E are various views of an exemplary anterior segment analyzer device according to some embodiments of this invention.
Figure 19B:
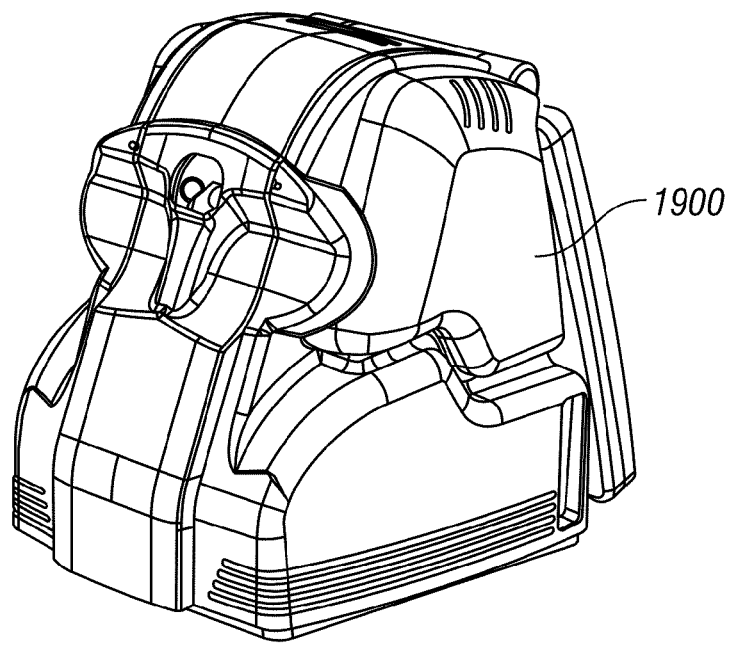
Figure 19C:
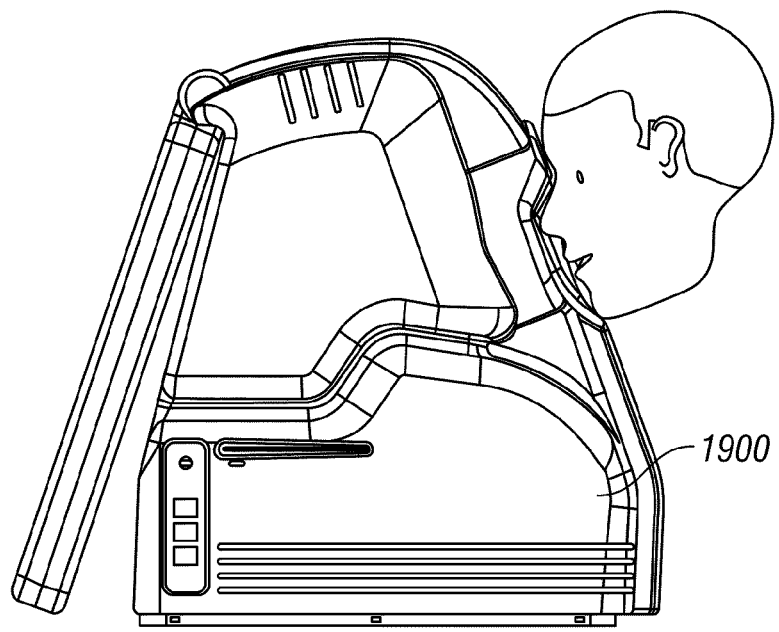
Figure 19D:
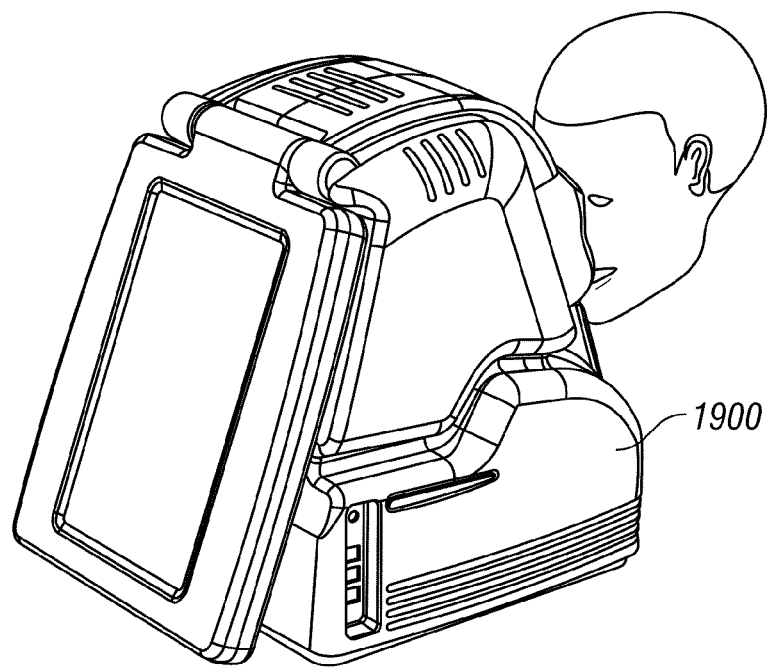
Figure 19E:
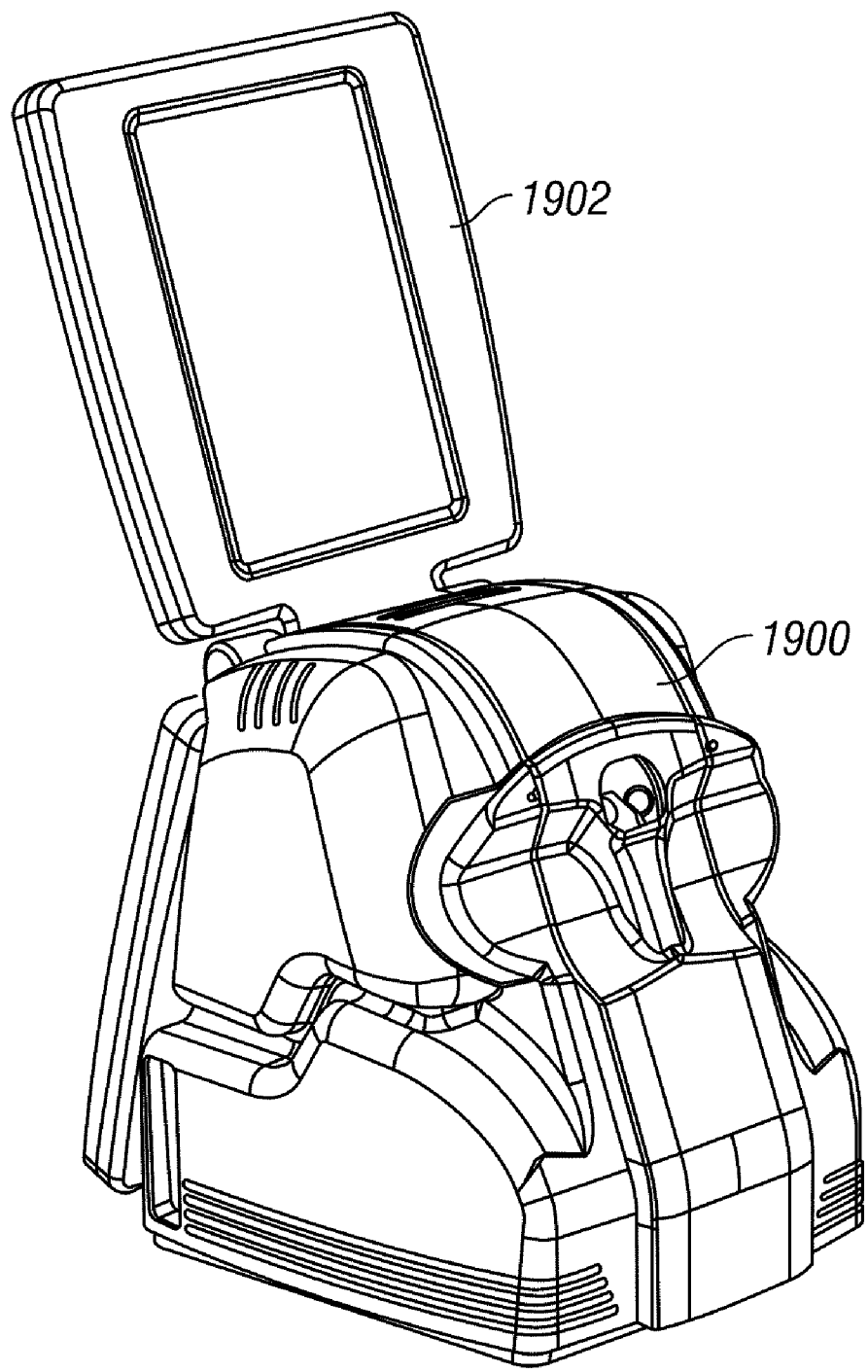

FIGS. 19A-19E illustrate various views of an exemplary ASA device 1900 configured in a compact housing in accordance with one embodiment. ASA device 1900 can incorporate many or all of the components of ASA device 800 and 1600, for example. As illustrated in FIGS. 19-19E, ASA device 1900 can also comprise a rotatable touch screen 1902.

Figure 20:
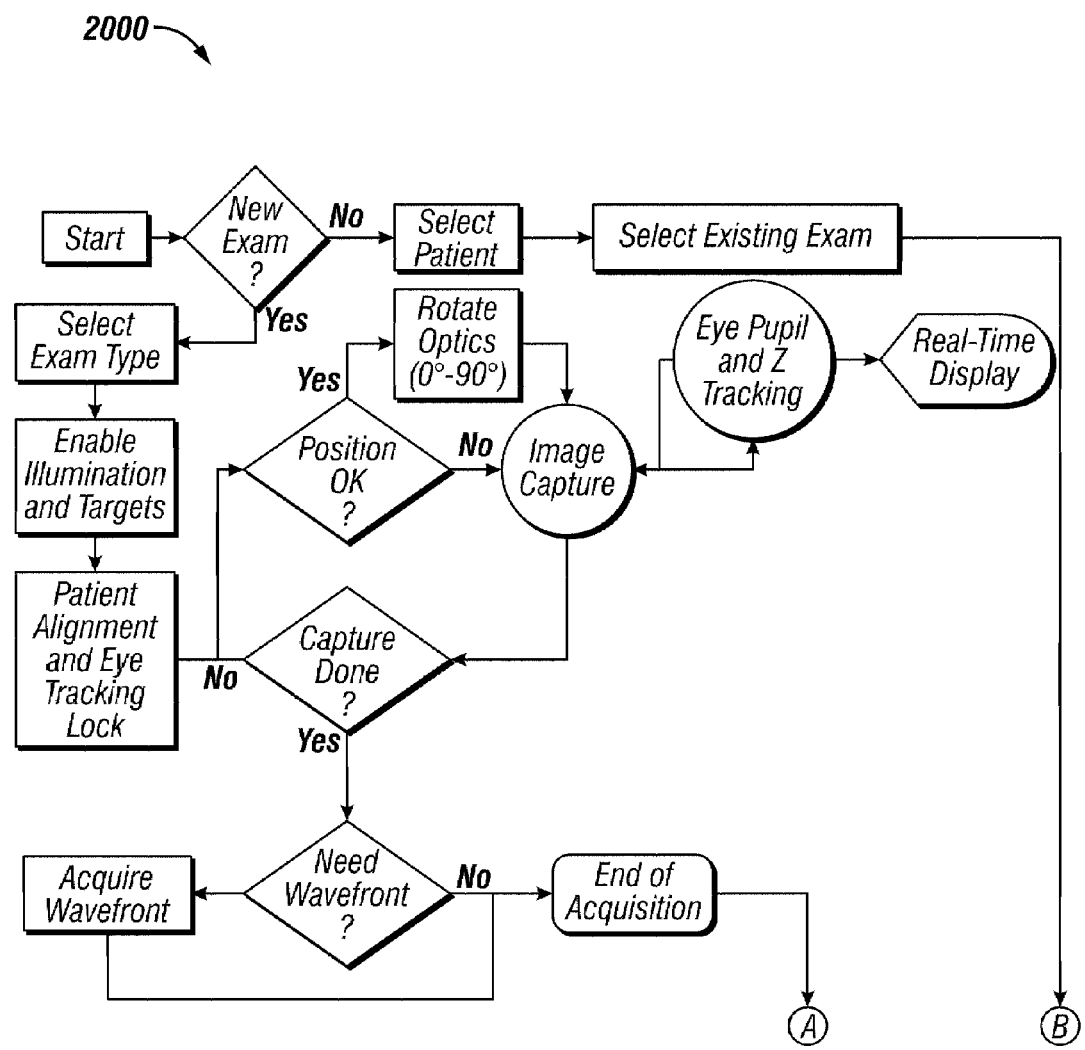
FIG. 20 is an exemplary device process flow diagram according to some embodiments of this invention.
Figure 20:
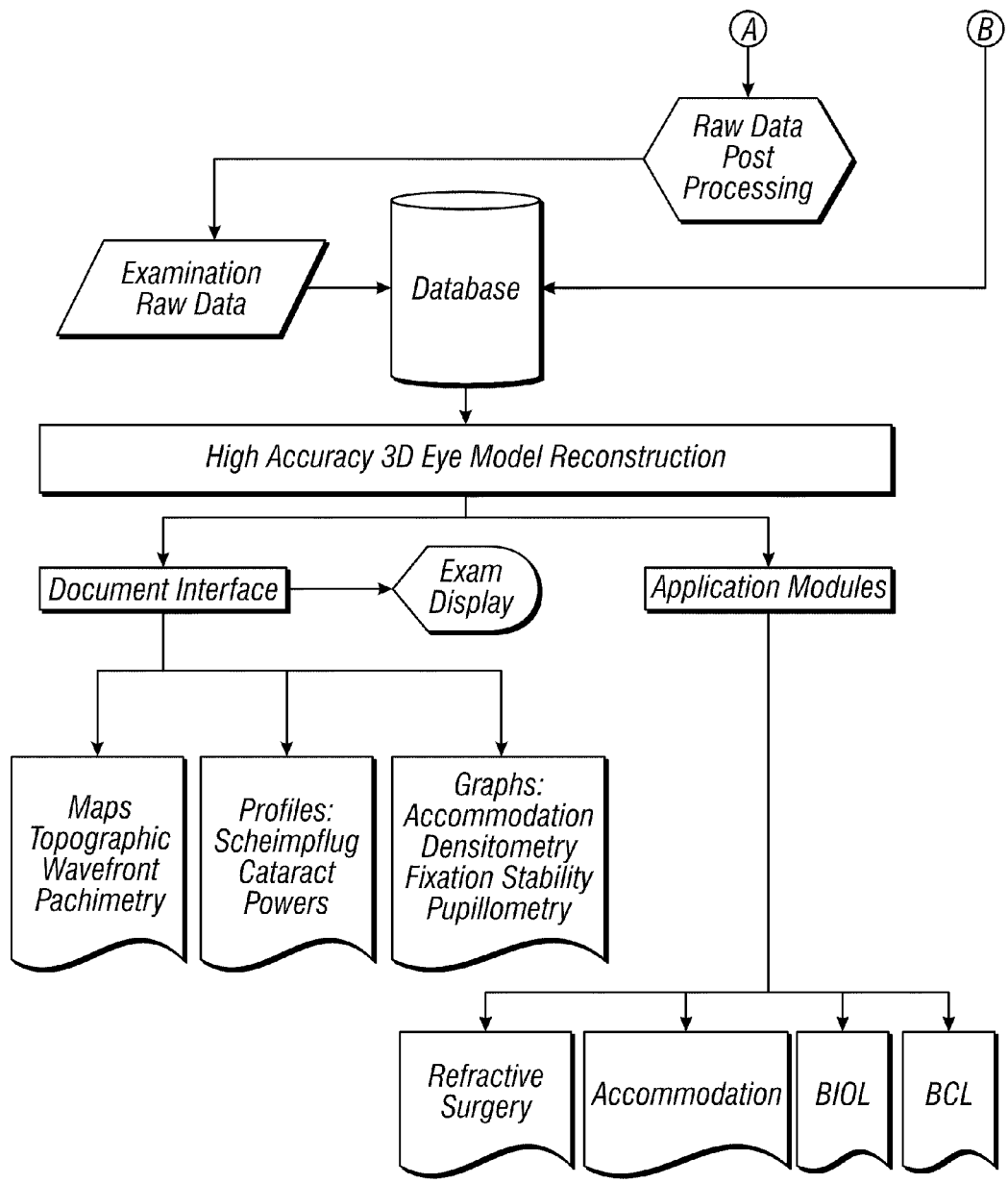

FIG. 20 is an exemplary flow diagram of an ASA device operational process 2000 in accordance with one embodiment. The various tasks performed in connection with process 2000 may be performed by hardware, software, firmware, or any combination thereof. It should be appreciated that process 2000 may include any number of additional or alternative tasks. The tasks shown in FIG. 20 need not be performed in the illustrated order, and process 2000 may be incorporated into a more comprehensive procedure or process having additional functionality not described in detail herein.

Figure 21:
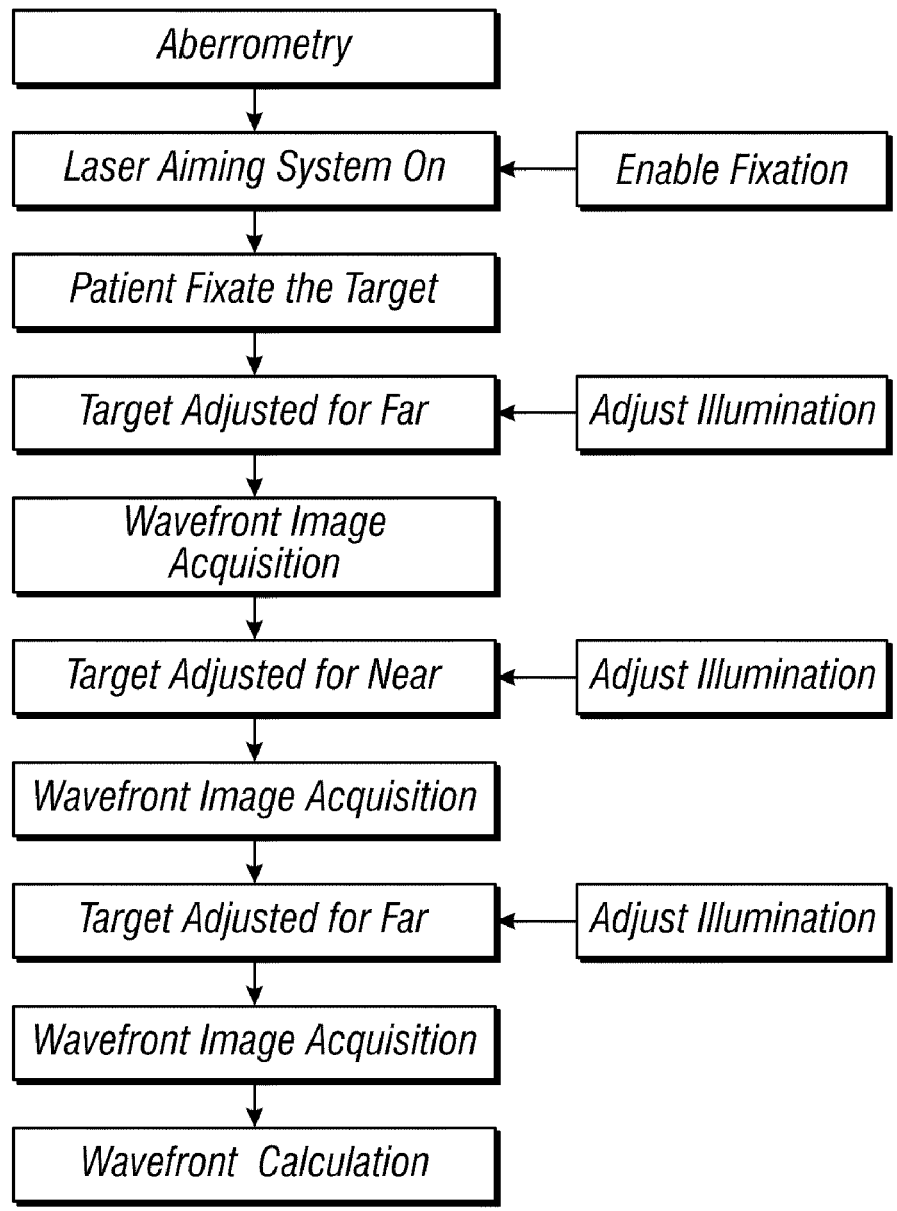
FIG. 21 is an exemplary flow diagram of an aberrometry examination according to some embodiments of this invention.

FIG. 21 is an exemplary flow diagram of an aberrometry examination process 2100 in accordance with one embodiment. The various tasks performed in connection with process 2100 may be performed by hardware, software, firmware, or any combination thereof. It should be appreciated that process 2100 may include any number of additional or alternative tasks. The tasks shown in FIG. 21 need not be performed in the illustrated order, and process 2100 may be incorporated into a more comprehensive procedure or process having additional functionality not described in detail herein.

Figure 22:
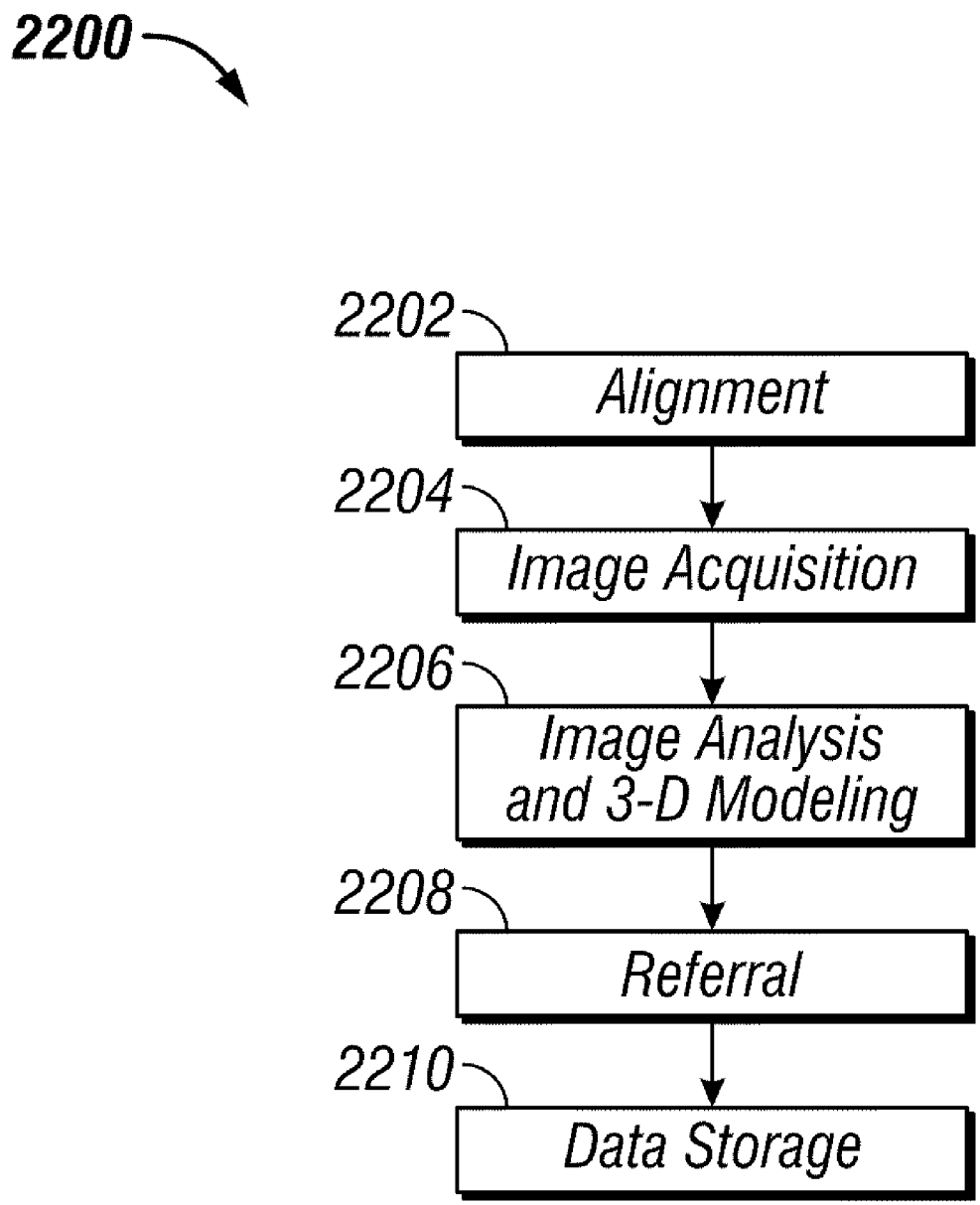
FIG. 22 is an exemplary flow diagram of an examination process according to some embodiments of this invention.

FIG. 22 is an exemplary flow diagram of an examination process 2200 in accordance with one embodiment. The various tasks performed in connection with process 2200 may be performed by hardware, software, firmware, or any combination thereof. It should be appreciated that process 2200 may include any number of additional or alternative tasks. The tasks shown in FIG. 22 need not be performed in the illustrated order, and process 2200 may be incorporated into a more comprehensive procedure or process having additional functionality not described in detail herein. For illustrative purposes, the following description of process 2200 may refer to elements mentioned above in connection with FIGS. 1-21.

ASA device 800 can be aligned at step 2200. Using information coming from a computer analysis of pupil camera system 1000 (FIG. 10), device 800 aligns the optical axis 806 of the device 800 with the visual axis 1504 (FIG. 15B) of an eye being examined using into the three-axis mechanical assembly 808.

At the alignment step 2002, the fixation target system 1200 also adjusts to an refractive error of the patient and, depending on the examination type, the fixation adjustable lens can be set for far, near or any intermediate vision.

Alignment step 2202 allows for precise alignment for examination of an eye and building a model of the eye in respect of the functional analysis performed by wavefront sensing system 1300, since two eye measurements (e.g., wavefront and Scheimpflug) can be performed at the same time or about the same time during the same or similar conditions and through the same visual axis.

Next, process 2200 proceeds to image acquisition step 2204. Depending on the specific examination type, ASA device 800 may acquire up to 360 images of a scheimpflug meridian. The Schiempflung camera system 802 can be continuously rotated for 90 degrees. This can allow acquisition of 360° imaging sections (within a pre-defined accuracy step) of the cornea around the visual axis using of the dual Scheimpflug camera system 802.

The following are exemplary types of examinations that can be performed at step 2204:

Single Image Examination: A single image, taken at 0° (parallel to the horizon) and used to extract AC (Anterior Chamber) biometric data such as AC depth, white-to-white and sulcus-to-sulcus distances, corneal pachimetry, crystalline lens dimensions and relations between biometric data and the visual axis.

Two Image Examination (Keratometry): Two images acquired at a main astigmatism axis (or at 0°) and secondary astigmatism axis (or at 90°). This examination can be used to obtain keratometric data.

Three or more Image Examination: a series of images that can be used to construct of a full three-dimensional model of the anterior part of the eye and to create topography and pachimetry maps of the cornea and the crystalline lens.

Video Stream Examination (Accommodation): In this mode the system acquires a video stream while the internal fixation and illumination systems are properly driven to re-create day/night far/near conditions. This examination mode provides accommodation and fixation profiles as well as visual axis displacement within different focusing/illumination conditions.

Aberrometry Examination: The examination is a functional evaluation of the examined eye wavefront. A laser illumination system is used to direct a luminous stimuli on the examined eye retina. The wavefront system 1300 can then receive and detect the out coming (reflected) wavefront from the examined eye pupil plane. The received wavefront can be plotted into an Aberrometry map.

Full Examination: All the above examinations are performed automatically.

Some of the above examinations, such as accommodation, can be performed with IR illumination in order to prevent the examined eye pupil from shrinking (non-midriatic). The light projection system 906 involved in the eye examination can be automatically selected between the blue light or IR light depending on what to capture: blue light for scheimpflug images; and IR light for accommodation examination.

Image analysis and three-dimensional modeling can be performed at step 2206. At this step, blue and/or IR light can be projected into the eye, illuminating the cornea and all the other optical elements of the eye (iris and crystalline lens) and providing a profile through the anterior segment of the eye. A dedicated ray tracing algorithm can be used to determine a geometry of the analyzed optical elements of the eye. To this end, process 2200 can correct distortion caused by scattered light refracted from intermediate optical surfaces.

After capturing Scheimpflug images (like images of FIGS. 17A and 17C, for example), an algorithm can be used to find edges of optical elements and calculate respective profiles, as illustrated in FIG. 17A, for example. If the eye examination generates a model of the examined eye, the profiles can be collimated and merged into a single, three-dimensional model.

Process 2200 then proceeds to referral step 2208. At step 2208, some or all profiles and maps can be displayed and included into an examination referral. In accordance with one embodiment, a broad set of clinical information pertaining to the examined eye can be provided, including any or all of the following:

Anterior chamber biometry (far/near+scotopic/photopic)
Corneal keratometry
Anterior cornea topographic map
Posterior cornea topographic map
Corneal pachimetry map
Anterior crystalline lens topography map
Posterior crystalline lens topography map
Aberrometry map
Accommodation profile (far/near+scotopic/photopic)
Pupillometry profile (far/near+scotopic/photopic)
Fixation Stability Profile (Far/Near+Scotopic/Photopic)
BIOL simulated implant
CL simulated fitting Data captured and generated during process 2200 can then be stored at step 2210. In accordance with one embodiment, captured data can be stored in its raw format with previews of the created maps and profiles. The data can be stored in computer 1602, or in some other local or remote data storage device.

While this invention has been described in terms of several exemplary embodiments, there many possible alterations, permutations, and equivalents of these exemplary embodiments. For example, the term "computer" does not necessarily mean any particular kind of device, combination of hardware and/or software, nor should it be considered restricted to either a multi purpose or single purpose device.

It should also be noted that there are many alternative ways of implementing the methods and apparatuses of the present invention. It is therefore intended that the following appended claims be interpreted as including all such alterations, permutations, and equivalents. In addition, as used herein, the terms "computer program" and "software" can refer to any sequence of human or machine cognizable steps that are adapted to be processed by a computer. Such may be rendered in any programming language or environment including, for example, C/C++, Fortran, COBOL, PASCAL, Perl, Prolog, assembly language, scripting languages, markup languages (e.g., HTML, SGML, XML, VoXML), functional languages (e.g., APL, Erlang, Haskell, Lisp, ML, F# and Scheme), as well as object-oriented environments such as the Common Object Request Broker Architecture (CORBA), Java™ (including J2ME, Java Beans, etc.).

Moreover, terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

What is claimed is:

1. An apparatus for imaging an eye, comprising:
 a first Scheimpflug imaging system having a first video camera and first optics configured to direct a first group of light reflected from an eye being examined into the video camera;
 a second Scheimpflug imaging system having a second video camera and second optics configured to direct a second group of light reflected from an eye being examined into the second video camera, the second Scheimpflug imaging system and the first Scheimpflug imaging system are positioned perpendicular to one another;
 a movable platform having at least a portion of the first Scheimpflug imaging system and least a portion of the second Scheimpflug imaging system fixedly connected to the platform so that the respective portions of the first and second Scheimpflug imaging systems move in accordance with any movement of the platform; and
 an eye movement tracking system comprising a third video camera and a third optics configured to direct a third group of light reflected from the eye into the third video camera,
 wherein the eye movement tracking system is capable of detecting movement of an eye away from an alignment position and wherein the movable platform is capable of moving to compensate for the detected eye movement so as to keep the eye in the alignment position.

2. The apparatus of claim 1, wherein the movable platform is configured to rotate approximately 90 degrees during an eye exam.

3. The apparatus of claim 1, further comprising a computer system having a processor and a memory unit, the computer system configured to receive video data from the first and second Scheimpflug imaging systems and the eye movement tracking imaging system and store the data in the memory unit.

4. The apparatus of claim 3, wherein the computer further comprises machine readable instructions stored in the memory unit, the machine-readable instructions including instructions for determining an eye movement and moving the platform in accordance with the eye movement so as to keep the eye in the alignment position.

5. The apparatus of claim 1, wherein each Scheimpflug imaging system is configured to capture images of an anterior eye segment.

6. The apparatus of claim 1, further comprising a wavefront aberrometer configured to produce a predefined wavefront, image the predefined wavefront on a patient's eye and receiving a reflected portion of the predefined wavefront from the patient's eye.

7. The apparatus of claim 1, further comprising a display, the display configured to display processed results of an eye imaging session.

8. The apparatus of claim 1, wherein the platform is capable moving in three dimensions in response to a detected eye movement.

9. The apparatus of claim 1, further comprising a first light source and a second light source emitting light onto the eye, wherein the first and second group of light comprises light from the first light source that was reflected from the eye and the third group of light is light from the second light source reflected from the eye.

10. The apparatus of claim 9, wherein the first light source produces a blue light and the second light source produces an inferred light.

11. The apparatus of claim 10, wherein the first and second light sources comprise respective LED, slit diaphragm and projection optics.

12. A method for analyzing an eye, comprising:
   imaging the eye using a first Scheimpflug imaging system and a second Scheimpflug imaging system;
   rotating the first and second Scheimpflug imaging systems about an optical path of the eye;
   imaging movement of the eye using an eye tracking imaging system; and
   moving both the first and second Scheimpflug imagining systems together in accordance with the detected eye movement so that the first and second Scheimpflug imaging systems continue rotating about the optical path of the eye.

13. The method of claim 12, further comprising capturing video data of the eye via the first and second Scheimpflug imaging systems.

14. The method of claim 13, further comprising processing the video data to produce a three-dimensional representation of a portion of the eye.

15. The method of claim 14, further comprising displaying the three dimensional representation on a display.

16. The method of claim 15, wherein each Scheimpflug imaging system captures an image of the eye at an angle of approximately 90 degrees from one another.

17. The method of claim 16, wherein each Scheimpflug imaging system is titled at approximately 40 degrees with respect to a tangential plane of the optical axis of the eye.

18. The method of claim 14, wherein the rotating step comprises rotating the Scheimpflug cameras 90 degrees about the optical axis.

19. An apparatus of imaging an eye, comprising:
   first Scheimpflug imaging means for obtaining an image of an eye being examined;
   second Scheimpflug imaging means for obtaining an image of an eye being examined;
   eye tracking means for tracking any movement of an eye being examined;
   movement means for moving the first and second Scheimpflug imaging means in accordance with any eye movement tracked by the eye tracking means.

* * * * *